(12) United States Patent
Gutman

(10) Patent No.: US 6,942,834 B2
(45) Date of Patent: *Sep. 13, 2005

(54) SYSTEM AND METHOD FOR OZONE CONTAINING PACKAGING FOR SANITIZING APPLICATION

(76) Inventor: Jose Gutman, 12643 Little Palm La., Boca Raton, FL (US) 33428

( * ) Notice: Subject to any disclaimer, the term of this patent is extended or adjusted under 35 U.S.C. 154(b) by 386 days.

This patent is subject to a terminal disclaimer.

(21) Appl. No.: 10/167,927

(22) Filed: Jun. 10, 2002

(65) Prior Publication Data

US 2002/0155027 A1 Oct. 24, 2002

Related U.S. Application Data

(63) Continuation-in-part of application No. 09/583,041, filed on May 30, 2000, now Pat. No. 6,403,033.
(60) Provisional application No. 60/136,885, filed on Jun. 1, 1999, now abandoned.

(51) Int. Cl.[7] .................................................. A61L 2/00
(52) U.S. Cl. .......................... 422/29; 422/24; 422/27; 422/28; 422/292
(58) Field of Search ........................ 422/29, 40, 28, 422/24, 27, 292; 219/294, 727; 250/455.11

(56) References Cited

U.S. PATENT DOCUMENTS

| | | | |
|---|---|---|---|
| 4,919,955 A | 4/1990 | Mitchell | |
| 5,011,699 A | 4/1991 | Mitsuda et al. | |
| 5,213,759 A | 5/1993 | Castberg et al. | |
| 5,227,184 A | 7/1993 | Hurst | |
| 5,352,467 A | 10/1994 | Mitchell et al. | |
| 5,405,671 A | 4/1995 | Kamin et al. | |
| 5,413,757 A | * 5/1995 | Kutner et al. | ................. 422/21 |
| 5,460,269 A | 10/1995 | Bayer | |
| 5,597,599 A | 1/1997 | Smith et al. | |
| 5,618,492 A | 4/1997 | Auten et al. | |
| 5,869,159 A | 2/1999 | Padilla | |
| 5,932,322 A | 8/1999 | Jones et al. | |
| 6,085,492 A | 7/2000 | Moller et al. | |
| 6,342,187 B1 | 1/2002 | Jacob et al. | |
| 6,403,033 B1 | 6/2002 | Gutman | |
| 2002/0122743 A1 | 9/2002 | Huang | |
| 2002/0150500 A1 | 10/2002 | Carman et al. | |
| 2002/0168287 A1 | 11/2002 | Eckhardt et al. | |
| 2003/0086818 A1 | 5/2003 | Holley, Jr. et al. | |
| 2003/0086821 A1 | 5/2003 | Matthews | |

FOREIGN PATENT DOCUMENTS

| | | |
|---|---|---|
| EP | 0 222 309 | 5/1987 |
| EP | 0 328 245 | 8/1989 |

* cited by examiner

*Primary Examiner*—Krisanne Jastrzab
(74) *Attorney, Agent, or Firm*—Jose Gutman

(57) ABSTRACT

A method and packaging system receive products and/or objects in a packaging storage volume, the packaging storage volume contains a first agent including oxygen that is energizably convertible by an ultraviolet radiation energy source to a sanitizing agent including ozone in the packaging storage volume, the sanitizing agent including ozone being transferable to the products and/or objects to provide at least one of a sanitizing, disinfecting, and sterilizing, application to the products and/or objects. The system also includes at least one of an incline, a ridged surface, ridged strip, a baffle structure, and other structure for providing rotational motion to the products and/or objects being stored in the packaging storage volume for exposing surfaces of the products and/or objects to the sanitizing agent comprising ozone and to the ultraviolet radiation energy. Additionally, a packaging storage control system is provided with timed intervals for exposure to sanitizing applications.

22 Claims, 22 Drawing Sheets

SYSTEM AND METHOD FOR OZONE CONTAINING PACKAGING FOR SANITIZING APPLICATION

CROSS-REFERENCE TO RELATED APPLICATIONS

This application is a continuation-in-part of, and claims priority from, prior U.S. patent application Ser. No. 09/583,041, filed on May 30, 2000, now assigned U.S. Pat. No. 6,403,033, the entire disclosure of which is herein incorporated by reference, and wherein such prior application was based upon, and claimed priority from, prior U.S. Patent Application No. 60/136,885, filed on Jun. 1, 1999, now abandoned, the entire disclosure of which is also herein incorporated by reference.

FIELD OF THE INVENTION

The present invention generally relates to using ozone to provide at least one of a sanitizing, disinfecting, and sterilizing, application to an object or product, and more particularly for a system and method for providing and containing a sanitizing agent comprising ozone gas in a packaging structure for an object or product to thereby transfer the sanitizing agent comprising ozone gas to the object or product while being located in the packaging structure and thereafter to prolong the at least one of sanitizing, disinfecting, and sterilizing, effect to the object or product in the packaging structure.

BACKGROUND OF THE INVENTION

Objects or products such as perishable food products, including meats, poultry, fish, fruits, and vegetables, or objects such as medical devices and instruments, or other objects that may be subject to infection or contamination by micro-organisms, viruses, and pathogens, typically require hygienic and sanitary conditions to be properly handled, packaged, and/or used. These types of objects or products are generally susceptible to contamination from micro-organisms such as bacteria, and from viruses, pathogens, and from other similar unsanitary contaminants. These objects are regularly subject to environmental exposure to contaminants such as micro-organisms, viruses, and other such contaminants thereby degrading sanitary and hygienic conditions for the objects or products.

Food products, for example, can seriously degrade in shelf life and can be dangerous for consumption under unsanitary states. Medical devices and instruments are likewise subject to contamination from many sources and can cause serious harm if used in unsanitary conditions. Cuts and wounds and other conditions of the body of animals and humans are similarly susceptible to external biological contaminants and micro-organisms and pathogens under unsanitary conditions which can cause infection, disease and other serious consequences if left unattended.

In the past, attempts to sanitize these types of objects have generally included washing and cleansing an object and then packaging and/or wrapping the object, which normally took place in special clean processing facilities. However, it is not always feasible or desirable to set up significant special facilities to sanitize such objects to desirable levels. For example, it may be desirable to package and/or wrap a food product at a convenient location where no special facilities are normally available such as at an office, a home, or even outdoors. Similarly, it may be desirable to package and/or wrap a medical device or instrument with no special medical cleansing facility being available or desirable for sanitizing the medical instrument before a subsequent use.

Regrettably, in most circumstances after providing sanitizing agents and cleansing facility to help clean and sanitize a product or object, subsequent poor handling by personnel typically results in re-contamination prior to final packaging of the product or object. This poor handling creates serious contamination hazards and transfer of disease to users and consumers of the products and objects being packaged under such conditions. Most commonly, an expensive special handling and processing facility is required to provide a sanitizing and/or sterilizing effect to an object or product. For example, irradiation processing of object and products requires very specialized and expensive equipment that is not readily usable in most environments.

With respect to perishable food products, such as meat, poultry, or fish, such products are normally packaged and re-packaged for subsequent use or distribution where at each stage of unpacking and re-packaging there is potential for introduction of contaminants, such as micro-organisms and viruses, and other pathogens, such as from *E-coli, samonella*, and *listeria* contamination, that can harm humans as well as seriously degrade the shelf life, increase perishability, and detrimentally impact human consumability, of such food products. The normal handling conditions at the different stages of product distribution, ultimately to handling by an end user, and further the re-packaging at each one of the stages, causes additional risk for contamination of such food products.

Additionally, even when sanitizing and/or sterilizing treatments are provided to products and objects to be packaged, commonly there are surfaces of the products and objects that may remain unexposed to the treatments. For example, the products and objects are typically located on a tray or other support structure as part of a packaging process. The surfaces of the products and objects that are in direct contact with the tray or other support structure will not be readily exposed to sanitizing and/or sterilizing treatments. Further, multiple products and/or objects being packaged together may make direct surface contact between the multiple products and/or objects. The surfaces of the multiple products and/or objects contacting with each other will likely remain unexposed to sanitizing and/or sterilizing treatments. Regrettably, after packaging of the products and/or objects, the unexposed surfaces will likely continue to carry contaminants, including microbes such as bacteria and viruses, that continue to pose contamination hazards to users and consumers of the products and/or objects. Therefore, sanitizing and/or sterilizing treatments of only the exposed surfaces may not remove the necessary amount of contamination to result in desired sanitary and/or sterile conditions for the packaged products and/or objects.

Food products, therefore, can include contaminants such as all sorts of micro-organisms, bacteria, and viruses. These contaminants can include, but are not limited to, bacteria, fungi, yeast, mold, mildew, and a variety of viruses. *E-coli* and *listeria* are pathogens that have gained much attention in the news where humans have been made sick and injured and have died as a result of contamination of food and water. Many of these types of contaminants can increase a rate of spoilage and reduce shelf life of food products as well as provide serious health hazards to humans that consume or come in contact with such products. Commonly, these contaminants are introduced to the surfaces of food products during processing, handling, and distribution.

Modern methods of packaging and cleaning food products, typically employed at food processing plants and factories, can reduce hazardous contaminants, such as micro-organisms, that can contaminate the surfaces of food products. These processing and packaging techniques include thermal processing, washing food products with chlorinated water, irradiation of food products, vacuum sealing packaging, low temperature storage, modified atmosphere packaging (or MAP), active packaging, and certain techniques for clean handling and packaging. Additionally, ozone bubbled in water has been used to wash and thereby disinfect chickens and other such food products and associated food processing plants and such specialized food handling environments. Ozone in such aqueous solution has been generally regarded as safe for use with the food supply. For example, most people are familiar with ozonated drinking water. However, these processes and techniques discussed above typically must be applied under strictly controlled environments in a processing plant and factory and usually employing special equipment and handling.

These specialized requirements for packaging such food products, although helpful in reducing contamination and enhancing shelf life of products, are generally expensive and only available in special environments such as in food processing plants and factories. Further, when the packaging is removed at a later point in a distribution channel and the food product is re-packaged for further distribution or for consumption at a later time, new contamination can typically be introduced to the food products thereby losing some if not most of the beneficial effects of the earlier clean handling and packaging at the factory. This subsequent re-packaging and handling normally does not benefit from special equipment and ultra-clean environment to re-package the food products with heightened sanitary conditions as in a food processing plant and factory.

In medical applications, where medical equipment and instruments need to be sanitized, unfortunately, conventional specialized equipment must be used to sanitize and disinfect the equipment or instruments to a satisfactory level, or possibly sterilize as necessary, for further use. This specialized equipment is usually expensive and the process for sanitizing, disinfecting, and/or sterilizing, tends to be time consuming significantly impacting the costs of medical services and the commercial viability of medical businesses. Additionally, this specialized equipment and processing is normally not generally available in all but specialized environments.

Accordingly, there is a need for a system and method to eliminate the disadvantages of the prior art as discussed above, and particularly to provide a sanitizing, disinfecting, and/or sterilizing, application to objects and/or products being packaged.

DESCRIPTION OF THE PREFERRED EMBODIMENTS

Figure 1:
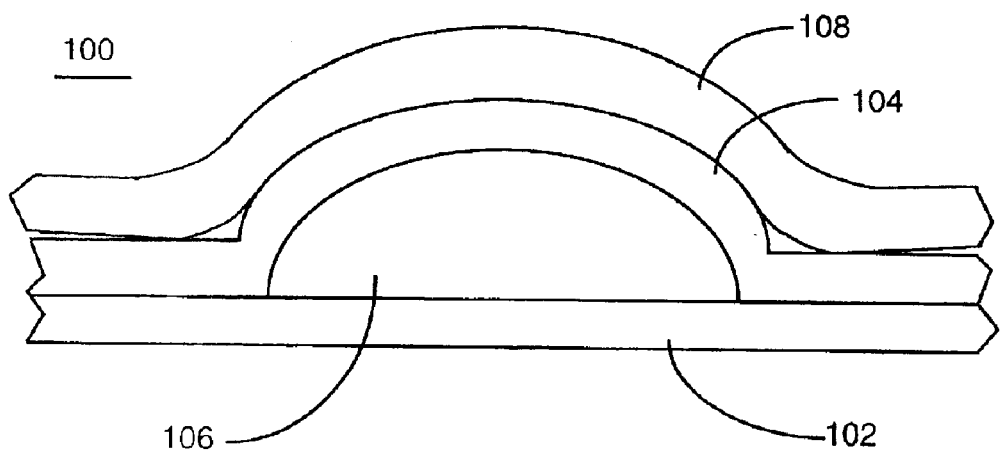

In accordance with a preferred embodiment of the present invention, and as illustrated in an exemplary configuration in FIG. 1, a sanitizing agent, preferably comprising a relatively high concentration of ozone gas to provide sanitizing, disinfecting, and sterilizing, treatment to an object or product, is captured or stored in a structure 100 for wiping, wrapping, and packaging, and for interaction with a surface of an object or product to provide sanitizing, disinfecting, and sterilizing, effect thereto. The structure 100 covers at least a portion of the surface of the object or product to provide a wrapping or packaging thereto and thereby extending the sanitary and hygienic state of at least the covered portion of the object or product.

The sanitizing agent comprising ozone gas is captured or stored in at least one store 106 in the sanitizing structure 100 as will be discussed in detail below. Although the structure 100 will be referred to as a sanitizing structure 100, it is understood that the structure 100 in all of its embodiments in accordance with the present invention can provide sanitizing, disinfecting, and sterilizing effects on objects or products for particular applications of the present invention. Therefore, unless specifically expressed otherwise, the term sanitizing structure shall include sanitizing, disinfecting, and sterilizing effects on objects or products in accordance with particular applications of the present invention.

As shown in FIG. 1, an exemplary multi-layer film or substrate structure 100 storing the sanitizing agent comprising ozone gas can be used. In this example, the sanitizing structure 100 comprises plastic film layers. However, other structure construction and arrangements that allow storage and/or transfer of a sanitizing agent comprising ozone gas are anticipated within the scope of the present invention, and as further discussed below.

Further, the term sanitizing agent comprising ozone gas is generally used herein to describe an agent that when transferred to a surface of an object or product at least provides the beneficial sanitizing, disinfecting, and sterilizing effects provided by ozone gas. Ozone gas has been shown very effective to sanitize, disinfect and sterilize equipment and processing facilities, as well as for ozonating drinking water. Ozone, in varying concentrations as a treatment for products and objects, can provide beneficial sanitizing, disinfecting, and sterilizing, effects thereto. Shortly after treatment, the ozone normally converts to a harmless composition usually resulting in oxygen and water associated with a treated product or object. For example, ozonated water additionally benefits from enhanced taste for human consumption.

The sanitizing agent comprising ozone gas, according to a preferred embodiment of the present invention, provides at least a reduction in microbial count as part of a sanitizing application. Further, in certain applications, such as for medical sanitizing or other product sanitizing, it is desirable that the sanitizing agent comprising ozone gas provide anti-viral and anti-pathogen properties to attack contaminants comprising viruses and other pathogens. Therefore, as anticipated by the embodiments of the present invention, and in accordance with specific applications thereof, the sanitizing agent comprising ozone gas provides anti-microbial properties to reduce microbial counts, including but not limited to reduction in bacteria, fungi, yeast, mold, and mildew, counts. Further, the sanitizing agent comprising ozone gas, according to alternative preferred embodiments of the present invention used in certain applications, additionally provides anti-viral properties to attack certain viruses. As is well known, ozone can exhibit such beneficial anti-microbial properties and anti-viral properties for specific applications of the embodiments of the present invention. Accordingly, the term sanitizing agent is used herein to comprise properties that can sanitize and disinfect, i.e., reduce microbial and viral counts, and/or sterilize, i.e., substantially minimizing counts thereof, with respect to an object or product being sanitized by the sanitizing agent comprising ozone gas and in accordance with specific applications. The term contaminants as used herein, therefore, includes such microbial and viral contaminants, and generally other invading contaminants, that can create unsanitary conditions, spoilage, and/or damage to objects or products.

Additionally, it should be clear that the structure 100 is usable such as for wiping, wrapping, and/or packaging, an object or product, and the structure 100 does not necessarily have to cover the entire surface area of the object or product. The structure 100 provides the beneficial sanitizing, disinfecting, and sterilizing effect while in close proximity to a surface of an object or product. In certain applications, for example, a wrapping structure 100 can cover a portion of a surface of an object to deliver sanitizing agent comprising ozone gas generally to the covered portion. In one exemplary embodiment of the present invention, a sanitizing bandage on a wound or cut on a patient's outer skin surface may only cover a portion thereof, e.g., a portion of the patient's skin area about the wound or cut, to provide beneficial sanitizing effect thereto.

In the current example, a first layer 102 in a multi-layer sanitizing structure 100 comprises a gas impermeable or low gas permeable plastic film which provides a substantial gas barrier to the sanitizing agent comprising ozone gas. It also provides a barrier from outside contaminants when the sanitizing structure 100 covers at least a portion of, and/or substantially encloses, an object such as a food product, or a medical instrument, or a patient's tissue or skin region such as about a wound or cut thereon.

A second layer 104 or substrate preferably comprises a highly gas permeable material, such as a high gas permeable plastic film, that allows transfer of the sanitizing agent comprising ozone gas. The gas permeability and transfer rate of the sanitizing agent comprising ozone gas can be substantially selected and configured into the second layer 104 to deliver a sufficient amount of sanitizing agent comprising ozone gas to the surface of an object or product and possibly continue delivery over a desired time interval.

The high gas permeable second layer 104, in one preferred embodiment of the present invention as shown in FIG. 1, comprises a plastic film formed with the first layer 102 to capture and store the sanitizing agent comprising ozone gas therebetween. The gas permeable plastic film of the second layer 104 allows transfer of the sanitizing agent comprising ozone gas from a stored or captured volume (a store) 106 through the second layer 104 to the opposing surface area thereof that is in close proximity and/or in direct contact with a surface area of an object or product requiring sanitizing effect thereto. This will be discussed in more detail below.

In the exemplary preferred embodiment of the present invention shown in FIG. 1, a third layer 108 is utilized to provide a substantial gas barrier to maintain the sanitizing agent comprising ozone gas captured between layer one 102 and layer two 104 of the sanitizing structure 100 until ready for use for sanitizing an object or product. The third layer 108, in an exemplary preferred embodiment, comprises a gas impermeable, or low gas permeable, plastic film that is mechanically coupled to the at least one store 106 and removable from the second layer 104 when ready to apply the sanitizing structure 100 such as to wrap or package an object or product.

For example, the third layer 108 can comprise a strippable plastic barrier that when removed from the second layer 104 allows the higher permeability of the second layer 104 to transfer the sanitizing agent comprising the ozone gas through the second layer 104. The permeability of the second layer 104 is selectable to provide a transfer rate that permits a user to apply the wrap and/or packaging to an object or product and then allows the sanitizing agent comprising ozone gas in at least one store 106 to continue to transfer onto the surface of the object or product to provide an extended sanitizing effect to the object or product. Additionally, the transfer rate may be selectable to vary across different portions of the structure 100 such as for particular wrapping and/or packaging applications, as will be discussed below.

Therefore, in a first preferred embodiment of the present invention, as shown in FIG. 1, the third barrier layer 108 comprises a removable or strippable film layer that is adhesively coupled to the second gas permeable layer 104 until ready to use. When ready to use, the third layer 108 is removed, such as by stripping apart the third layer 108 from the remaining structure 100, including the second and first layers 104,102, forming the at least one store 106. Preferably, the third removable layer 108 is a plastic film that is strippable off the outer surface of the second gas permeable layer 104 thereby removing the barrier effect and releasing the transfer of the sanitizing agent comprising ozone gas through the second gas permeable layer 104.

Figure 2:
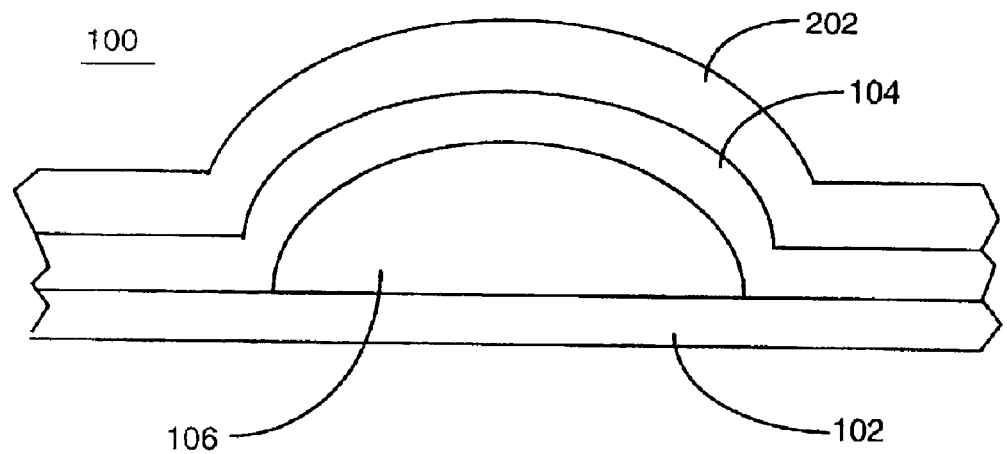
FIGS. 1 and 2 are cross-sectional side views of alternative wrapping and/or packaging structures according to preferred alternative embodiments of the present invention.

In a second preferred embodiment of the present invention, as shown in FIG. 2, the wrapping and/or packaging structure 100 comprises a barrier third layer 202 that is substantially formed on the outer surface of the second gas permeable layer 104. For example, the third layer 202 may comprise a very thin film, liquid, gel, or wax, that readily dissolves upon contact with surface fluids of an object. In this way, the barrier third layer 202 is removable upon use, such as by soluble interaction with an object or product, thereby allowing the sanitizing agent to transfer from the at least one store 106 across the gas permeable second layer 104 in close proximity and/or making surface contact with the object or product thereby providing the sanitizing benefit to the object or product.

Figure 3:
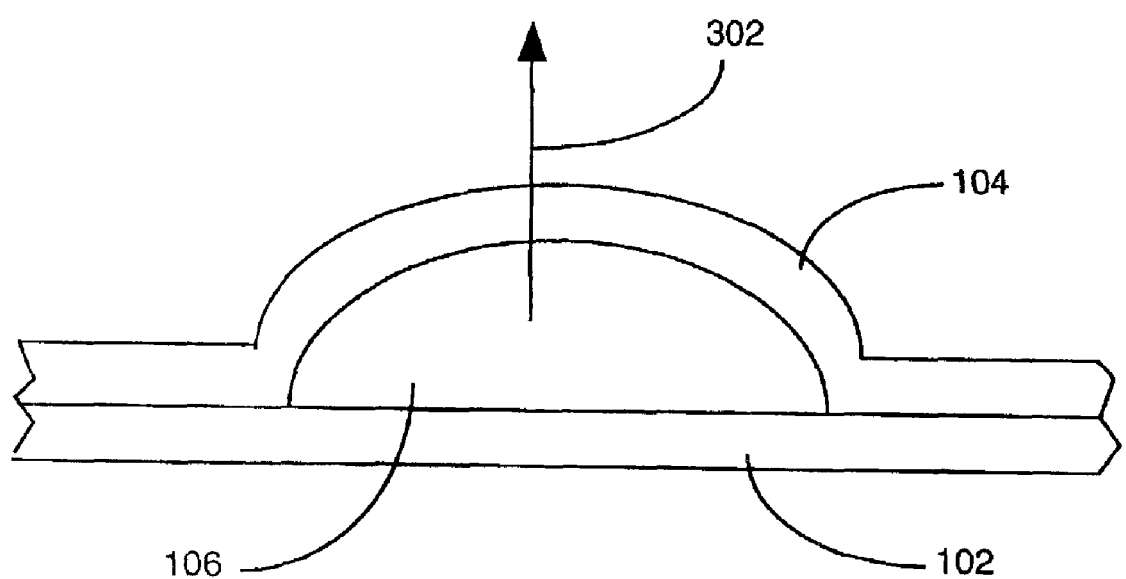
FIG. 3 is a cross-sectional side view of a wrapping and/or packaging structure according to a preferred embodiment of the present invention.
Figure 4:
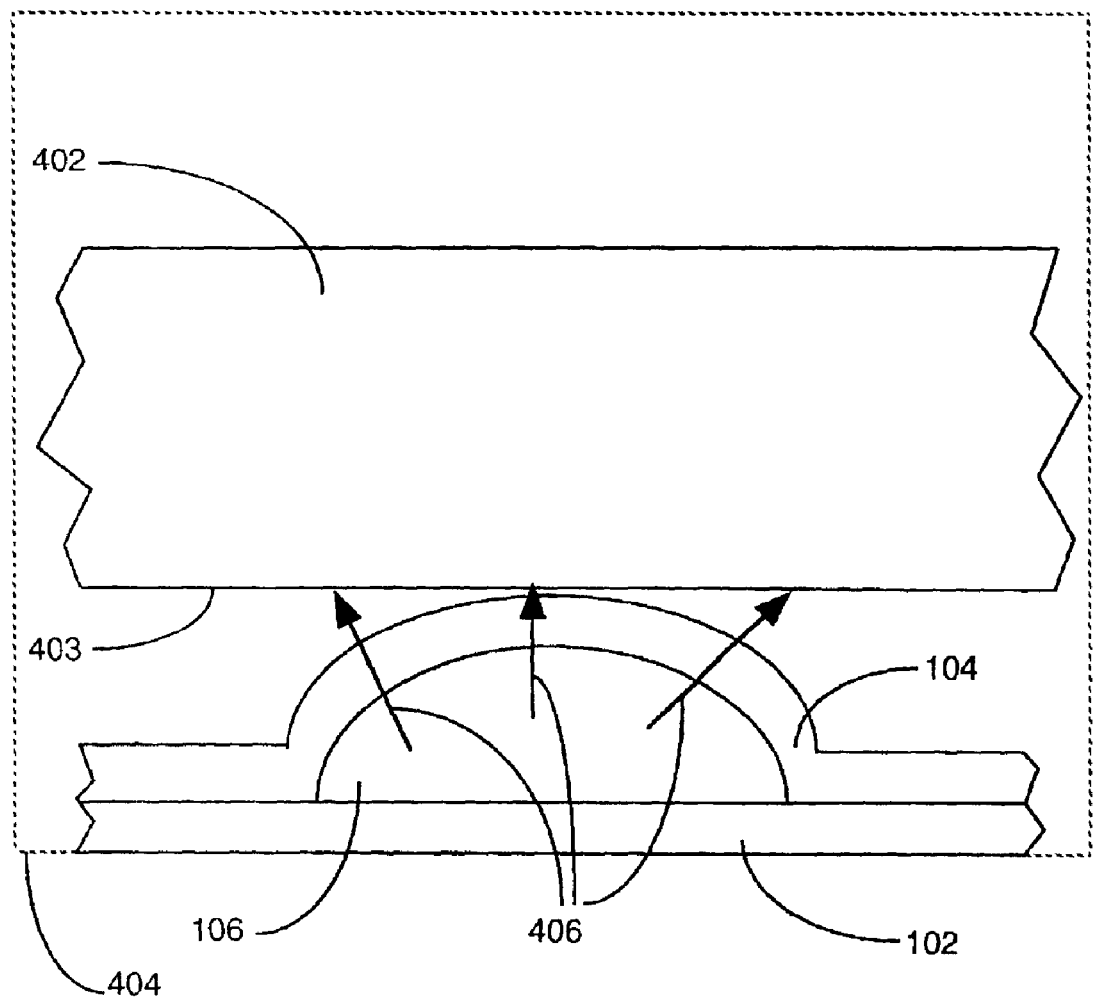
FIG. 4 is a cross-sectional side view of a packaged and/or completely wrapped object according to a preferred embodiment of the present invention.

As shown in FIG. 3, the third layer 108,202 (from previous FIGS. 1 or 2) has been removed from the second layer 104 allowing the second layer 104 to be exposed and to be located in close proximity to an object to transfer (as shown by arrow 302) sanitizing agent comprising ozone gas through the second layer 104 to the surface of the object. In a packaging application, as illustrated in FIG. 4, a surface 403 of an object 402 is located in close proximity to layer two 104 with layer three removed. The wrapping and/or packaging structure 100 substantially encloses the product or object 402 to provide a substantially sealed enclosure 404 about the object or product 402 that is being sanitized by the sanitizing agent transferring 406 through the second layer 104. As shown in FIG. 4, after the object 402 is substantially enclosed and protected by the gas impermeable (or low gas permeable) outer layer, which is layer one 102, the enclosed object or product 402 can benefit from the extended sanitizing effect of the sanitizing agent comprising the ozone gas because outer contaminants are generally prevented from invading and contaminating the sanitized object 402 in the enclosure 404 due to the outer protective layer one 102.

Figure 5:
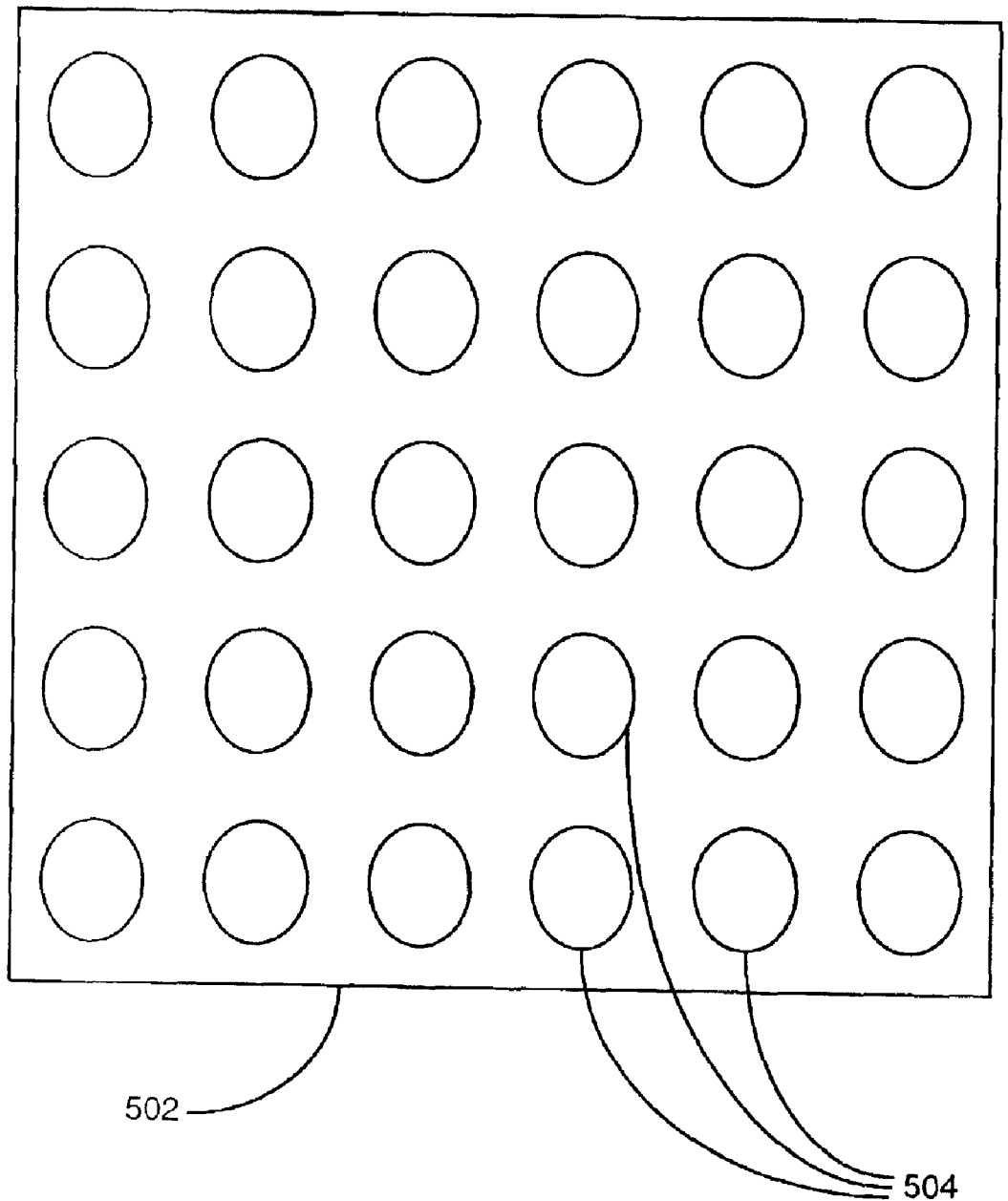
FIG. 5 is a top plan view of an exemplary sheet comprising a plurality of stores in accordance with a preferred embodiment of the present invention.

As shown in FIG. 5, a collection of stores 504 can be created on a sheet or film area 502 to provide sanitizing effect about the surface of an object or product to be sanitized. For example, a sheet of film wrap or packaging 502 can include a plurality of stores 504 that substantially capture sanitizing agent comprising ozone gas for use to sanitize an object. After the third barrier layer is removed from the second gas permeable layer of the sheet, the plastic film sheet 502 can be used to wrap and substantially enclose an object or food product and thereby provide sanitizing agent to the object while maintaining the outer contaminants away from the sanitized surfaces of the object enclosed within the wrapped plastic film sheet 502. Layer one 102 of the plastic film sheet provides a substantial barrier to these external contaminants thereby extending the sanitizing benefit provided to the object within the wrap or packaging in close proximity to the second layer 104 which is gas permeable.

In a preferred alternative embodiment of the present invention, the strippable third layer 108 is located in strips over select stores 106 such that the sheet 502 can be re-used by releasing certain stores 106 for each application of the sanitizing sheet 502. Each time that the sheet 502 is to be used, a certain collection of stores 106 can be released to allow the transfer of sanitizing agent comprising ozone gas from the released stores 106. Those stores 106 that remain covered by a sealing layer 108, will also be activated and contain the sanitizing agent comprising ozone gas. However, ozone in these stores will convert back to oxygen if not released and used in a particular sanitizing application. Thereafter, another at least one strip of the strippable third layer 108 can be removed from the sheet 502 to release another collection of stores 106 for another application (re-use) of the sheet 502. By applying a subsequent exposure to UV energy, for example, those stores that have been subsequently released will contain the sanitizing agent comprising ozone gas and will transfer their contents to an object or product in a sanitizing application re-using the sanitizing sheet 502. This is a significant advantage of the present invention that allows re-use of the structure 100 for repeated sanitizing applications.

In one preferred alternative embodiment, a plurality of strips 108 are arranged about the sheet 502 with one or more strips 108 in association, such as indicated by a common attribute such as a common colorization treatment to indicate the association. The at least one strip 108, as indicated such as by a common color of the at least one strip 108, is then removed by a user of the sanitizing sheet 502 to re-use the sheet 502 in a sanitizing re-application by activating and releasing a plurality of stores 106 covered by the at least one strip 108. For a subsequent sanitizing application (re-use of the sheet 502), for example, the user would remove a second at least one strip 108 of a different color. For example, a blue colored association of strips 108 would be removed for a first sanitizing application of the sheet 502, and then a yellow colored association of strips 108 would be removed by the user for a second sanitizing application (re-use of the sheet 502). As can be appreciated by those of ordinary skill in the art, other attributes of the association of the at least one strip 108 can be used to indicate grouping for common release in sanitizing applications and re-use of the sanitizing sheet 502. For example, patterns and/or colors on or about an association of strips 108 can be used as indicators of a common use for a sanitizing application. Also, shapes of the at least one strip can be used to indicate a common grouping for a common use in a sanitizing application of the sheet 502.

Figure 6:
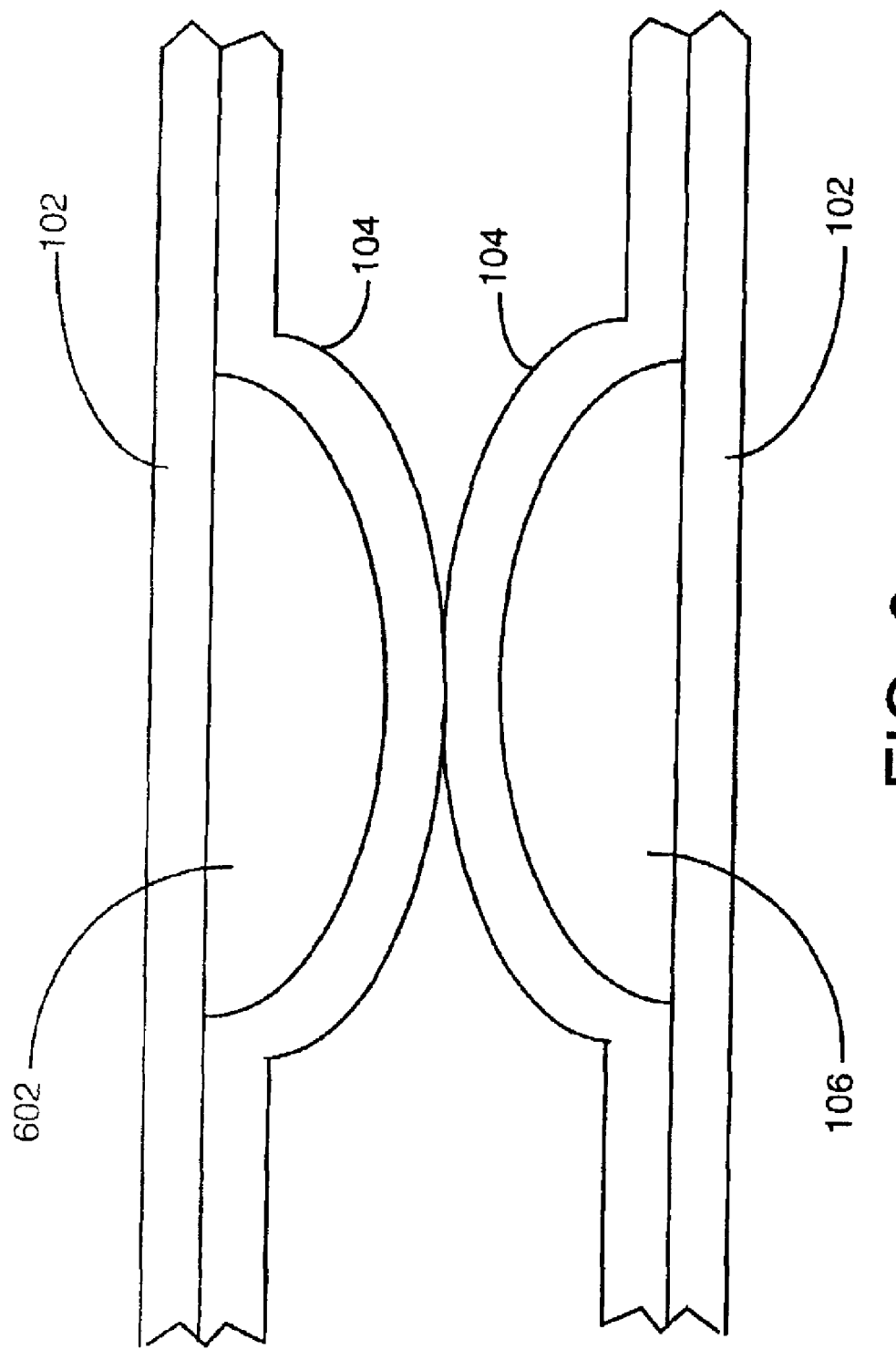
FIGS. 6 and 7 are cross-sectional side views of alternative wrapping and/or packaging structures according to the preferred embodiments of the present invention.

Referring to FIG. 6, an alternative preferred embodiment of the present invention comprises the first layer 102 and the second layer 104 similar to the discussion above, while omitting the third layer 108 as a separate independent structure. Consequently, the removable barrier effect of the third layer 108, namely until the product or object is to be wrapped or packed for sanitizing, is provided by a separate portion of the second layer 104 that is located in close proximity and/or mechanically coupled and/or in direct contact with the other portion of the second layer 104. This is shown in FIG. 6, where the sheet providing the at least one store 106 of the sanitizing agent comprising the ozone gas is folded onto itself, thereby making contact between two surfaces of the inner second layer 104 within the fold of the sheet. This contact between portions of the second layer 104 provides sufficient barrier effect to maintain the sanitizing agent comprising the ozone gas reliably stored in the storage regions of the sheet of wrap or packaging, until initial use with an object.

The barrier effect is aided by surface contact between the two portions of the second layer 104 and, where the contact is minimal or merely in close proximity between the two portions, a captured gas or fluid can provide sufficient barrier pressure to the second layer 104 thereby retaining the stored sanitizing agent in the stores 106,602. A gas, such as comprising a high concentration of carbon dioxide being captured in-between the two portions of the second layer 104 folded into itself may provide significant gas pressure upon micro-perforations (not shown in this figure) of the second layer 104 to reduce any significant transfer of the sanitizing agent from the at least one store 106 through the micro-perforations of the second layer 104. Additionally, the high concentration of carbon dioxide gas atmosphere is a substitute for an air or other nitrogen containing atmosphere. It may be desirable, in certain applications, to minimize the nitrogen content of an atmosphere that may be subjected to energizing ultra-violet light energy and could result in undesirable nitric oxides or nitrous oxides, as will be discussed in detail below.

This configuration for the wrapping and/or packaging structure 100 allows easy storage and quick and efficient deployment of a wrap and/or packaging sheet ready to provide the sanitizing effect of the sanitizing agent comprising ozone gas to at least a portion of an object being wrapped and/or packaged. When the sheet is unfolded and the gas permeable second layer 104 is spread apart from the two contacting or close proximity portions it essentially activates the gas permeable layer to begin to transfer the sanitizing agent from the stores 106,602. The transfer rate normally is not instantaneous and can be selected to a time duration permitting a user of such a wrap and/or packaging ample time to utilize the wrap and/or packaging on a product to be sanitized.

In prior art packaging methods, such as modified atmosphere packaging (MAP) or active packaging, a food product is introduced into a packaging and then a modified atmosphere is introduced into the packaging upon seal. The modified atmosphere typically is introduced by some form of injection or similar process after the product has been packaged. This, unfortunately, has the consequence that normally only a certain portion of the product is exposed to the modified atmosphere upon packaging. This is mainly due to the product being pre-packaged in a container and then the modified atmosphere being introduced from one side, usually the top side, of the packaging thereby exposing only that immediate side of the product to the modified atmosphere. However, other significant sides of the package and food product are normally not immediately exposed to the modified atmosphere. The modified atmosphere generally has to travel through the packaged product to reach some of the other surfaces of the product. Therefore, any contaminants on surfaces of the product not directly exposed to the modified atmosphere may not be significantly affected by the modified atmosphere.

Figure 7:
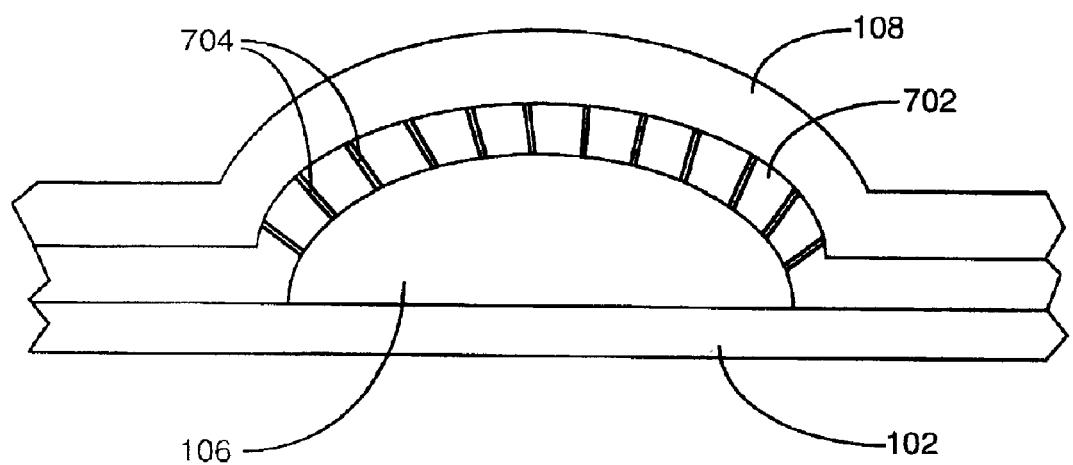

Referring to FIG. 7, an alternative preferred embodiment of the present invention comprises a modified second layer 104 in the wrapping and/or packaging structure 100. To increase the transfer rate of the sanitizing agent comprising the ozone gas at least a portion of a second layer structure 702 preferably includes micro-perforations 704 that are preferably selectively located to enhance the transfer rate of the at least one store 106 when the sanitizing structure 100 is in use with an object or product to be sanitized. By selectively locating the micro-perforations 704 the transfer rate of individual stores 106 and/or the transfer rate associated with different portions of a wrap and/or packaging structure 100 can be selected for particular applications. Note that the second layer 104 can include a gas permeable layer, or micro-perforations, or both, to select a transfer rate for sanitizing agent comprising ozone gas for particular applications.

The micro-perforations 704 create channels from the store side of the second layer 104 containing the sanitizing agent comprising the ozone gas to the opposing side of the second layer 104. When the second layer 104 is exposed to close proximity to the surface of an object, the micro-perforations 704 transfer the sanitizing agent from the at least one store 106 to the surface of the object thereby providing the beneficial sanitizing effect to the object. The micro-perforations 704 preferably are located about the store area of the second layer structure 702 to allow the transfer of sanitizing agent when the wiping, wrapping, and/or packaging structure 100 is used to sanitize the object. In certain applications, a wiping action utilizing the structure 100, such as via micro-perforations 704, can quickly provide sufficient sanitizing agent comprising ozone gas to a surface of an object or product to provide substantial beneficial sanitizing effect to the object or product. Thereafter, the structure 100 can be removed, or alternatively can be used as a wrap or package to provide extended sanitizing benefit to the object or product. For example, cuts or wounds may benefit from a sanitizing wiping structure 100 that can be conveniently used to provide sanitizing benefit and then can optionally be used to wrap or bandage the cuts or wounds to extend cleanliness and to enhance a healing process.

Micro-perforations 704 located towards the center portion of the store 106 may come in contact with different surfaces of the object than micro-perforations located towards the outer periphery portions of the store 106. In this way therefore, by strategically locating the micro-perforations 704 and channels across the at least one store 106, the at least one store 106 can deliver significant sanitizing agent to the surfaces of the object that are exposed to the channels 704 that can transfer sanitizing agent. This is particularly helpful for objects that have uneven surfaces and may come in contact with some but not all of the micro-perforations and channels 704 thereby allowing through the open channels 704 the transfer of sanitizing agent. Note that the third layer 108 is a removable layer such as generally described with respect to FIG. 1 and/or FIG. 2, and/or as may be recognized by those skilled in the art.

Figure 8A:
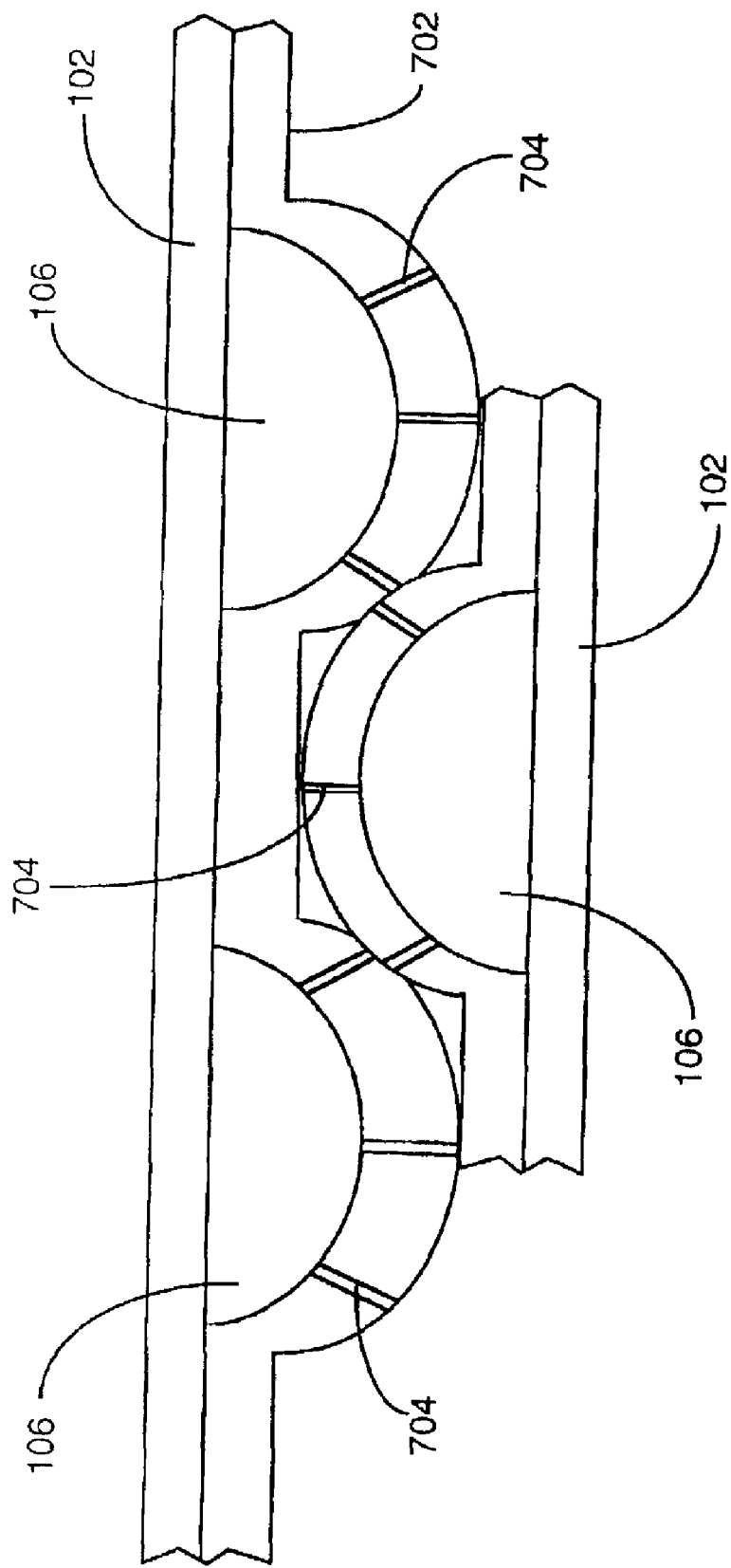
FIGS. 8A and 8B illustrate cross-sectional side views of an alternative wrapping and/or packaging structure according to a preferred embodiment of the present invention.
Figure 8B:
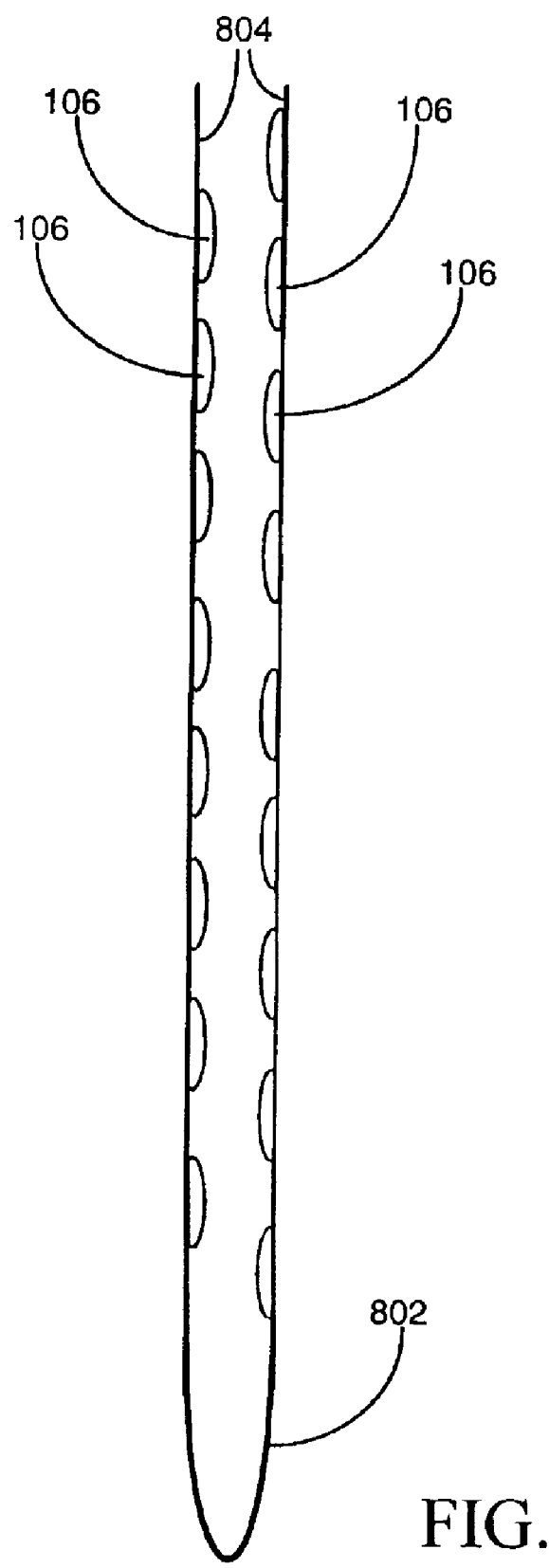

Referring to FIGS. 8A and 8B, an alternative preferred embodiment of the present invention is shown. A plurality of stores 106 are preferably arranged in a staggered pattern in a sheet of wrapping or packaging material such that, when folded to locate two portions 804 of the sheet in close proximity to each other, as shown in FIG. 8B, the stores 106 are located in between each other, in a staggered arrangement, to reduce the overall height of the folded sheet 802 thereby enhancing the storage and portability of the wrapping and/or packaging structure due to the overall size or height thereof. Additionally, interlaced stores 106 can make surface contact with other stores 106 from the opposing portion of the sheet thereby helping to seal and contain the micro-perforations 704 and channels 704 to prevent the sanitizing agent from transferring out of the stores 106 until ready to use. When ready to use, the sheet 802 is unfolded and the stores 106 are separated such that the micro-perforations and channels 704 are not sealed or contained. This allows the sanitizing agent comprising the ozone gas to begin transferring from the stores 106 through the channels and micro-perforations 704 in the second layer 702 and to permeate about, and make contact with, the surface of the object to be sanitized.

Figure 9:
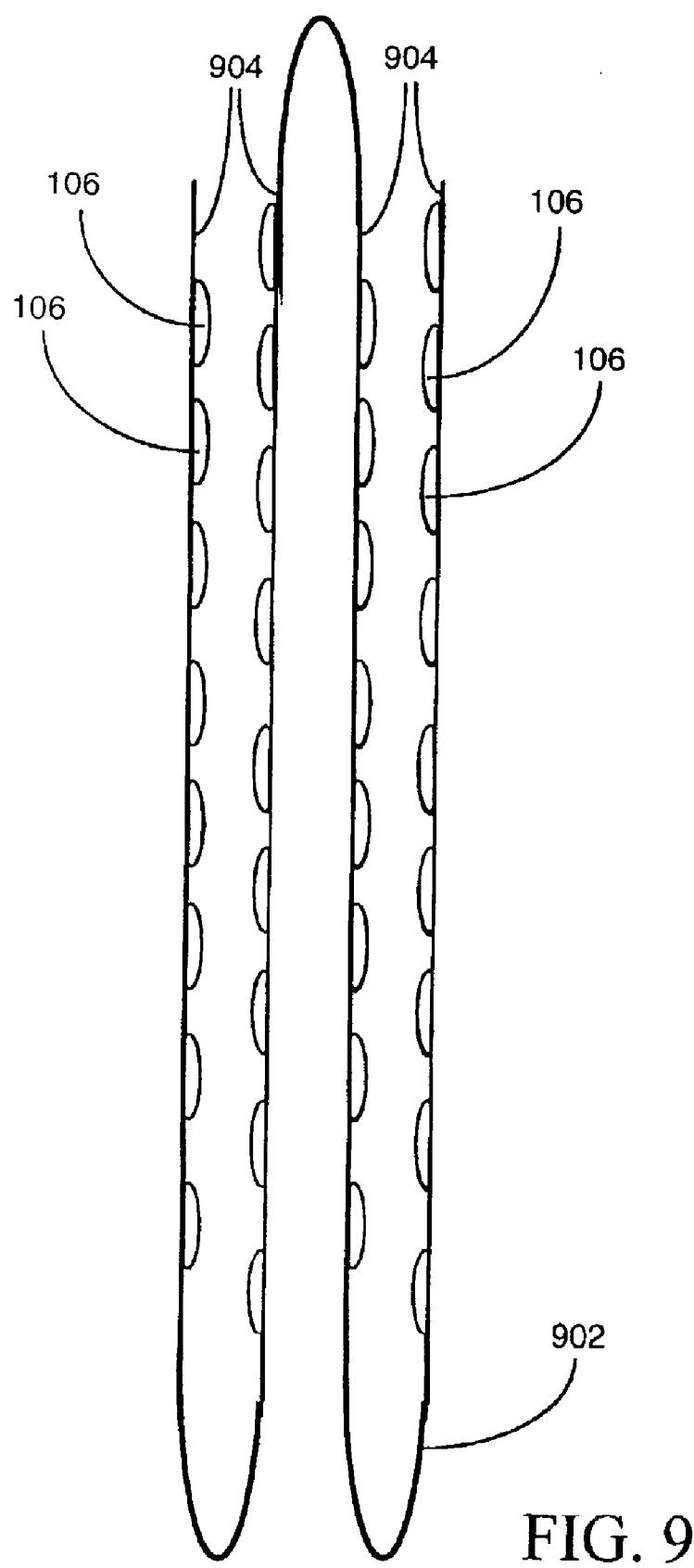
FIG. 9 is a cross-sectional side view of an alternative wrapping and/or packaging structure according to a preferred embodiment of the present invention.

In one alternative embodiment, the wrap and/or packaging can be stored in a fan folded multi-layer structure 902 as shown in FIG. 9. The plurality of stores 106 face each other via a plurality of portions 904 of the second layer 702 that are fan folded to face each other. The barrier to each portion of the second layer 702 is a corresponding opposing portion of the second layer 702 that is fan folded to create a temporary barrier layer thereby substantially maintaining the sanitizing agent comprising ozone gas in the stores 106 until ready to use. When the wrap or packaging material is ready to use, a length of the fan folded wrap and packaging material is unfolded thereby exposing the second layer 702 and separating the opposing portions of the second layer 702 thereby allowing the sanitizing agent comprising ozone gas to be released from the stores 106. The object is wrapped and/or packaged with the wrapping and packaging structure such that the second layer 702 is in contact with, or close proximity to, the surface of the object thereby transferring sanitizing agent to the surface of the object to provide the sanitizing effect thereto. Once the object is wrapped and/or packaged within the wrapping or packaging structure, the gas impermeable (or low gas permeable) layer one 102 maintains and extends the sanitizing effect to the object while providing a barrier to external contaminants and unsanitary conditions thereby enhancing and prolonging the beneficial sanitizing effect to the object.

Preferably, prior to use, the fan folded wrap or packaging structure has been folded in a controlled atmosphere environment comprising a high concentration of carbon dioxide gas and preferably comprising a minimal amount, such as a near zero amount, of nitrogen gas. In this way, between the layers of the fan folded wrapping and/or packaging structure is substantially captured an atmosphere comprising a high concentration of carbon dioxide and a very low or near zero concentration of nitrogen gas.

As an alternative exemplary storage arrangement to that shown in FIGS. 8A, 8B, and 9, a spool of the wrap and/or packaging structure 902, or sheet 802, contains the plurality of stores 106 wound in layers of the structure 902 about the spool. The plurality of stores 106 are maintained sealed in between the windings of the sheet 802 wound on the spool where the second layer 702 is in substantial contact with the first layer 102. For example, in one application, the contact can seal and contain the micro-perforations 704 and channels 704 to prevent the sanitizing agent from transferring out of the plurality of stores 106 until ready to use. The entire wound sheet 802 about the spool can be exposed, for example, to ultraviolet energy when ready to use. A portion of the sheet 802 is unwound from the spool and the stores 106 on that portion are separated from the sealing layer of the wound sheet 802. In one example, a seal is removed from micro-perforations and channels 704 on that unwound portion of the sheet 802 which allows the sanitizing agent comprising the ozone gas to begin transferring from the stores 106 through the channels and micro-perforations 704 in the second layer 702. The portion of the sheet 802 can be used, for example, to wrap a product and thereby the sanitizing agent comprising ozone gas can make contact with the surface of the wrapped product to be sanitized.

According to a preferred embodiment of the present invention, the at least one store 106 is filled with a gas atmosphere comprising a relatively pure oxygen gas with near zero concentration of nitrogen gas. A mixture of approximately 30% carbon dioxide and 70% oxygen, for example, can remain stable in the at least one store 106 until ready to be used in a sanitizing application. However, higher or lower concentrations of oxygen gas may be desired for particular applications. Then, ultraviolet energy radiation, preferably with peak energy in the 185 nm wavelength range and with significantly reduced energy in the 253 nm wavelength range, can be radiated to the at least one store 106 to energize and convert the oxygen gas to ozone gas. This process activates the contents of the at least one store 106 to provide a sanitizing agent therein.

The oxygen gas is a much more stable form of gas than the ozone gas. The oxygen gas therefore has a long shelf life and can be stored relatively reliably in the at least one store 106 until ready to be used.

It is a well known principle that ozone gas can be formed from oxygen gas by increasing the energy of the oxygen to create the ozone gas. The general process of converting oxygen gas to ozone gas is a well understood process. By using an energy source, such as an ultraviolet radiation energy source or an electrical corona discharge radiation energy source, oxygen gas can efficiently and relatively quickly (in seconds) be converted to ozone gas. Accordingly, an energy source that converts oxygen to ozone, as anticipated by those of ordinary skill in the art, may be usable in accordance with the preferred embodiments of the present invention. Additionally, the oxygen gas and the ozone gas may exist in a gas atmosphere, and alternatively in a fluid atmosphere, in the at least one store 106. Accordingly, an agent contained in the at least one store 106 may comprise gas, and alternatively fluid, that includes the oxygen for conversion to the ozone. The oxygen can be energized and converted to ozone to provide a sanitizing agent in the at least one store 106. The oxygen can be energized by the energy source as discussed above to provide the sanitizing agent comprising ozone in the at least one store 106.

For example, a source of ultraviolet energy, e.g., UV radiation about 185 nanometer (nm) wavelength, is efficient at converting oxygen to ozone. However, UV radiation about a 253 nm wavelength range, although exhibiting anti-bacterial killing properties, tends to be destructive of ozone. That is, ozone will quickly convert back to oxygen when energized by the about 253 nm wavelength ultraviolet radiation. Therefore, according to a preferred embodiment of the present invention, the UV energy source preferably has a peak radiation output about 185 nm wavelength and exhibits little or no radiated energy about the 253 nm wavelength range.

Certain UV sources, such as utilizing elements comprising mercury gas or other such gas, can be very effective at radiating UV energy at the desired 185 nm wavelength range. Additionally, there are new and very efficient and reliable UV sources based on ultraviolet and blue laser technologies that emit radiation about the desired 185 nm wavelength range. For example, there are electronic devices, such as laser diodes based on gallium nitride, that can provide a reliable source for the desired ultraviolet energy radiation. These laser diodes have been measured to provide UV radiation during thousands of hours of reliable use. Additionally, a UV filtering barrier, e.g., a sheet of quartz material with UV filtering properties added thereto, can be located between the UV energy source and the target at least one store 106. Such a UV filter preferably provides a bandpass of the UV energy radiation, as necessary in a particular application, to allow pass through of the desired 185 nm wavelength range while significantly blocking or attenuating the undesired 253 nm wavelength range.

When other gases and chemicals are present with the oxygen during this conversion process, such as when ozone is generated from ambient air, then other by-product resulting gases and chemicals may be undesirably created along with the ozone gas. This is the case, for example, when ozone gas is created utilizing conventional air ozonators that draw in filtered ambient air and energize it to create ozone. Unfortunately, such other undesirable gases and/or chemicals as nitric oxide and/or nitrous oxide may also be created. These unfortunate by-products typically exhibit strong acidic effects which can damage certain sensitive surfaces of objects and products to be sanitized. Therefore, in a preferred embodiment of the present invention, the ozone, with it's desirable anti-microbial, anti-viral, anti-pathogen, and sanitizing effect, is created from an agent that comprises a high concentration of pure oxygen and a very low or preferably a near zero concentration of nitrogen. In this way, the conversion process from oxygen to ozone precludes additionally creating the undesirable by-product gases and chemicals such as from the combination of the nitrogen with the oxygen during the conversion process while attempting to create ozone. This will substantially preclude the creation of these undesirable byproduct gases and chemicals. According to a preferred embodiment, a substitute gas such as carbon dioxide is used to complement the oxygen gas in a balanced atmosphere allowing a selected concentration of ozone from pure oxygen to be created as part of a sanitizing agent, as will be discussed in more detail below.

According to the preferred embodiment, a sanitizing wrapping or packaging structure 100 includes at least one store 106 that contains a sanitizing agent preferably comprising pure ozone gas. That is, pure ozone gas is preferably made from an atmosphere containing oxygen gas and with very little or near zero nitrogen gas thereby precluding much of the undesired by-product gases as discussed above.

Figure 10:
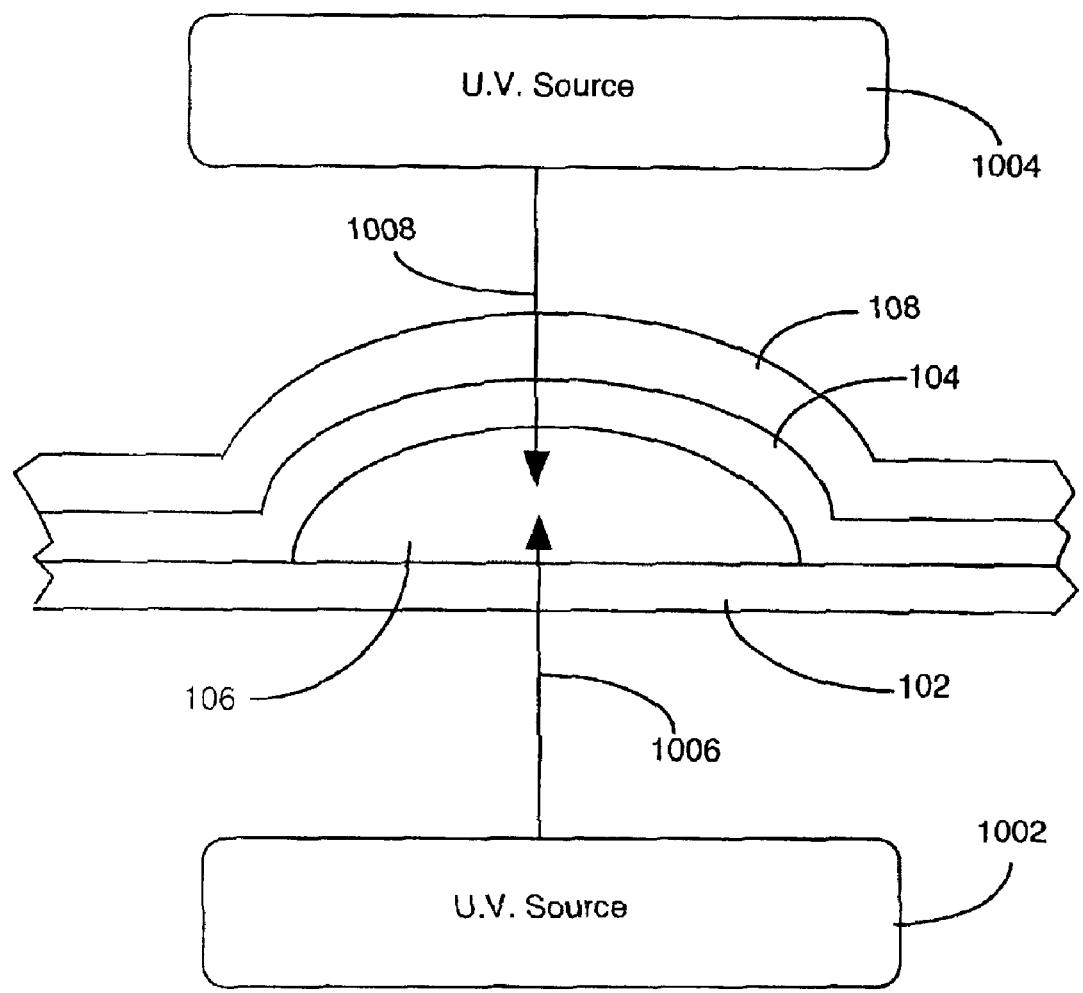
FIG. 10 is a cross-sectional side view of an exemplary wrapping and/or packaging structure exposed to ultraviolet light energy according to a preferred embodiment of the present invention.

The at least one store 106 is created preferably between the first and second layer 102,104, to contain a gas atmosphere that preferably initially includes a high concentration of oxygen gas and a minimal or no significant presence of nitrogen gas. Carbon dioxide gas, for example, can be included in the at least one store 106 with the high concentration of oxygen gas. The wrapping and/or packaging structure 100, in a preferred embodiment, is transparent (not opaque) to ultraviolet light allowing ultraviolet light energy to pass through the first layer 102, or the second layer 104, or both, as illustrated in FIG. 10. Plastic film that is non-UV inhibiting is desired for efficient delivery of the UV energy to the at least one store 106. Avoid UV-inhibiting additives being added to the plastic film. The ultraviolet light energy stimulates the oxygen increasing the energy of the oxygen gas and causing the oxygen to convert to ozone gas. This is typically a very quick (in seconds) process.

In one alternative embodiment of the present invention, a plastic film used for layer one 102 and a gas permeable plastic film used for layer two 104 comprises a gas containing flexible film structural arrangement for providing the at least one store 106. The at least one store 106 initially contains a high concentration of oxygen atmosphere with preferably no significant amount of nitrogen gas mixed therein. The structural arrangement permits ultraviolet light radiation 1006,1008, as shown in FIG. 10, from at least one UV source 1002,1004, to activate and energize the oxygen contained within the at least one store 106 to create a high concentration of pure ozone gas atmosphere within the store 106. Further, the absence of nitrogen gas precludes the energizing of the atmosphere from creating undesirable by-product gases and chemicals such as nitric oxide or nitrous oxide in the store 106.

By storing the more stable oxygen gas in the at least one store 106, the wrapping and/or packaging structure 100 with the at least one store 106 benefits from a long shelf life and reliable storage. At a point in time within a reasonable proximity to a desired time for using the wrap and/or packaging material for sanitizing an object, the oxygen containing wrapping and/or packaging material can be subjected to the ultraviolet light energy to activate and energize the oxygen to create the sanitizing agent comprising pure ozone gas within the at least one store 106. The ozone gas remains contained in the at least one store 106 for a significant amount of time, such as minutes and/or possibly hours, before the wrapping and/or packaging structure 100 is to be used to provide sanitizing effect to an object. Ozone gas is normally in an unstable state. After a maximum storage time, the ozone gas typically loses its reactive characteristics and converts back to the stable form of oxygen gas. However, this maximum storage time provides plenty of time for using the sanitizing wrap and/or packaging structure 100 to transfer the sanitizing agent comprising the ozone gas to an object to be sanitized. Therefore, the wrap and/or packaging structure 100 containing the pure oxygen in the at least one store 106 can be activated and/or energized by an energy source, such as the ultraviolet radiation source, to provide the sanitizing agent comprising ozone gas in the at least one store 106.

The energizing of the oxygen to create the ozone can be done prior to a sanitizing application on an object, as well as while the object is covered, wrapped or packaged by the wrapping and/or packaging structure 100. In the latter case, the object is already in close proximity and/or packaged within the wrap and/or packaging structure 100 while the UV source energizes a captured atmosphere comprising the oxygen to provide the sanitizing agent comprising the ozone gas. However, it is desirable to energize and convert the oxygen to ozone while contained in the at least one store 106. For example, in certain applications it may be desired to avoid potential contamination with nitrogen gas from ambient air during the energizing of the oxygen to create the pure ozone. As another example, the UV energy can potentially cause damage to sensitive surfaces of certain objects. As illustrated by such exemplary cases, it may be preferable to have the oxygen be energized and converted to pure ozone gas while captured in the at least one store 106. Then the wrapping and/or packaging structure 100 with the sanitizing agent comprising ozone gas can be used to sanitize the object.

Ozone may also be created from the oxygen in the ambient air surrounding the at least one store 106 while energizing the oxygen in the at least one store. For example, a UV source will deliver UV energy both to the gas in the at least one store 106 and to the surrounding ambient atmosphere. This ozone from ambient air may be undesirable in certain applications. For example, the ozone created from ambient air may detrimentally affect the air quality in an enclosed work area for people and animals.

Figure 16:
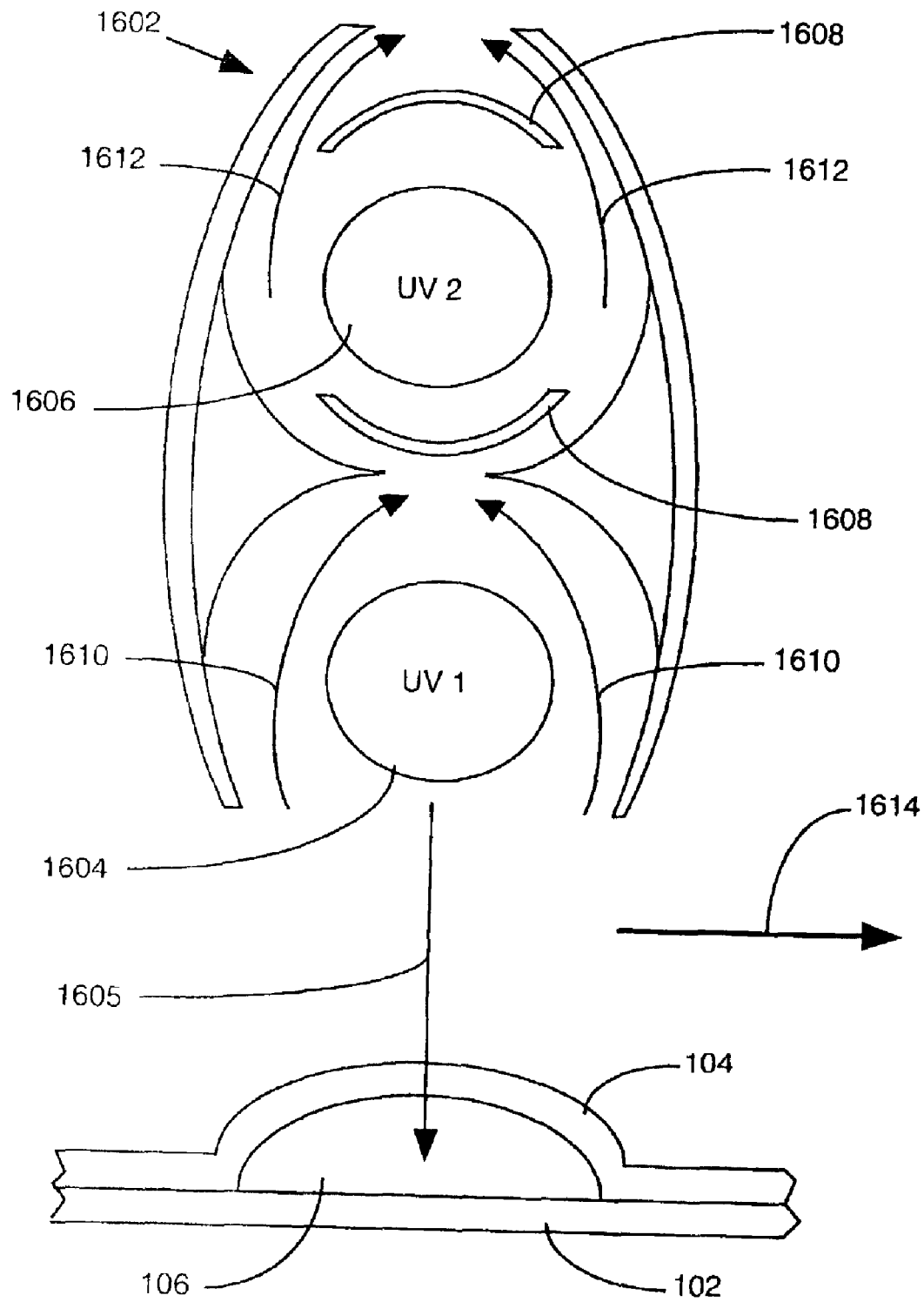
FIG. 16 is a cross-sectional side view illustrating an exemplary construction and arrangement of an ultra-violet radiation source device, in accordance with a preferred embodiment of the present invention.

As illustrated in FIG. 16, a novel construction and arrangement for a device providing at least one UV source utilizes the fact discussed above that the UV radiation about the 253 nm wavelength range will quickly convert ozone gas to harmless oxygen gas. In a work area, as shown, a structure comprising at least one store 106 receives UV radiation energy 1605 at about the desired 185 nm wavelength range. This tends to also energize and create undesired ozone gas 1610 in the ambient atmosphere surrounding the work area. It is desired to convert the oxygen gas in the at least one store 106 to ozone gas while at the same time converting ozone gas 1610 that may be present in the ambient atmosphere surrounding the work area to harmless oxygen gas 1612.

As illustrated in FIG. 16, an exemplary device 1602 includes a first UV source 1604 that provides the desired UV energy radiation 1605 at about the 185 nm wavelength range. This radiated energy 1605 energizes the oxygen gas in the at least one store 106. Additionally, the radiated energy 1605 energizes the oxygen in the ambient atmosphere and creates undesired ozone gas 1610. According to this example, the first UV source 1604 tends to heat the ambient atmosphere with the ozone gas 1610. This gas mixture tends to rise due to convection as shown. The device 1602 includes a set of baffle chambers 1608 that allow the gas atmosphere with the ozone gas 1610 to enter an inner chamber containing a second UV source 1606 that provides UV energy radiation at about the 253 nm wavelength range. The second UV source 1606 converts ozone gas 1610 to harmless oxygen gas 1612 that by convection exits through the upper portion of the set of baffle chambers 1608 in the device 1602. This second UV source 1606 is shielded by the walls of the set of baffle chambers 1608 from radiating on the work space where the structure comprising the at least one store 106 receives UV radiation energy 1605 from the first UV source 1604. The first UV source 1604 therefore radiates UV energy at the at least one store 106 at the desired 185 nm wavelength range to create ozone gas while the second UV source radiates within the inner chamber to convert ozone gas 1610 to harmless oxygen gas 1612. This device, as shown in FIG. 16, can energize the structure with the at least one store 106 as the structure is moving 1614 relative to the device 1602. The device 1602, therefore, can be located on a stationary base, e.g., where the structure with the at least one store 106 can be moved 1614 either manually or mechanically such as by a conveyor mechanism, or alternatively the device 1602 can be moved 1614 (either manually or mechanically) across a work space to energize and activate the sanitizing agent in the at least one store 106. Although the device 1602, in this example, is illustrated utilizing convection energy to draw the ozone gas 1610 through the device 1602, it should become obvious to those of ordinary skill in the art that other means of moving the gas 1610 through the device are intended within the scope of the present invention. For example, an oscillating fan, a piezoelectric vibrator, or other such vibrator associated with the device 1602 can move gas through the device 1602 to pass the ozone gas 1610 through the inner chamber for the second UV source 1606 to convert the ozone gas 1610 to oxygen gas 1612. Also, a tube (not shown) coupled to the upper portion of the device 1602 can provide an exhaust path for guiding the gas 1612 away from the work space.

Additionally, in certain packaging applications oxygen atmosphere is not desired for any extended period of time to be in contact with the object or product being packaged. For example, oxygen can oxidize and degrade food quality over time. Accordingly, it may be desirable to utilize an oxygen scavenger means in combination with the wrapping and/or packaging structure 100 according to the present invention to provide the sanitizing benefit of the sanitizing agent comprising ozone gas to the object or product and thereafter remove any remaining oxygen from the packaging or wrapping to reduce the undesirable effects on the object or product. Oxygen scavenging packaging technology is generally well understood by those skilled in the art. Oxygen scavenging product technologies such as oxygen scavenging sachets, labels, coatings, and polymers, are commercially available for use in different applications.

For example, a UV energy activated oxygen scavenger technology is commercially available, such as from Cryovac, a division of the Sealed Air Corporation, located in New Jersey, USA. The technology is offered under the packaging system called OS1000. It utilizes a polymer film that is part of the packaging, such as in a MAP application, and a UV light activating system to trigger the oxygen scavenging properties of the polymer when desired.

In such an exemplary application, and according to an alternative embodiment of the present invention, at least a portion of layer one 102 of the wrapping and/or packaging structure 100 comprises the polymer film with the UV energy activated oxygen scavenging properties. The UV energy can be applied to the wrapping and/or packaging structure 100 in accordance with the present invention to activate the sanitizing agent comprising ozone gas and to activate the oxygen scavenging properties of the polymer. The wrapping and/or packaging structure 100, in close proximity and/or in contact with an object or product, then transfers the beneficial sanitizing effect to the surface of the object or product. This is a relatively faster process than the oxygen scavenging process of the activated polymer.

For example, the sanitizing effect can be transferred in seconds from the at least one store 106 to the object or product, while the oxygen scavenging process of the polymer operates much slower, such as taking hours or days to effectively remove residual oxygen from the wrapped and/or packaged product or object. In this way, for example, a single exposure to UV energy can both activate the sanitizing agent comprising ozone gas in the at least one store 106 and activate the oxygen scavenging properties of the polymer. The wrapping and/or packaging structure 100, when activated with the UV energy, can wrap and/or package the object or product and transfer thereto the sanitizing agent comprising ozone gas and additionally can gradually scavenge the residual oxygen after sanitizing the object or product to reduce the undesirable effects of long term exposure to oxygen.

Additionally, as can be appreciated by one of ordinary skill in the art, the polymer film discussed above can be alternatively arranged with respect to the wrapping and/or packaging structure 100 for different applications, and optionally utilizing more than one exposure to UV energy, to activate the sanitizing agent comprising ozone gas to sanitize the object or product and then to substantially scavenge the remaining oxygen from a wrapped and/or packaged object. For example, the polymer film can be arranged as a portion of the wrapping and/or packaging structure 100, or as a separate sheet, where a first exposure to UV energy activates the sanitizing agent comprising ozone gas to sanitize the object or product and a second exposure to UV energy activates the oxygen scavenging properties of the polymer film to extract the remaining oxygen from the wrapped and/or packaged object or product.

Figure 11:
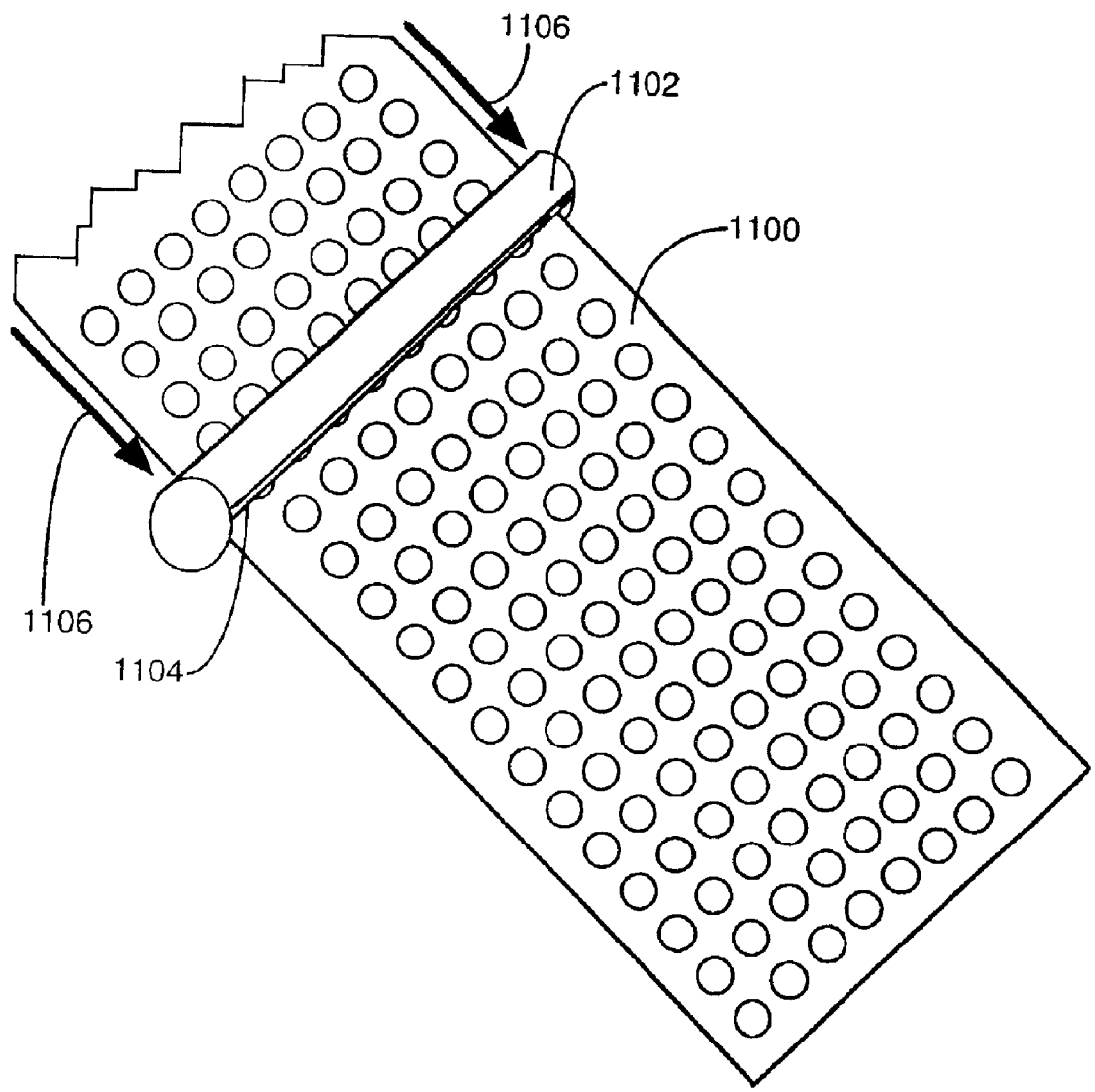
FIG. 11 is an isometric view of a portion of a sheet and an exemplary ultraviolet light energy source energizing at least one store of the sheet to provide sanitizing agent comprising ozone gas therein according to a preferred embodiment of the present invention.

For example, the polymer film can be arranged as a portion of the wrapping or packaging structure 100, such as at least one strip or flap portion or the wrapping and/or packaging structure 100. The UV energy can be selectively exposed on the portion of the wrapping and/or packaging structure 100 to activate the sanitizing agent comprising ozone. For example, an ultraviolet wand or bar 1102, as shown in FIG. 11, can have selected portions of the UV energy source blocked to prevent exposure of UV energy over certain portions of the sheet. Then, the object or product is wrapped and/or packaged and the sanitizing agent is transferred to the object or product. Then, a second exposure to UV energy over the entire sheet wrapping and/or packaging the object can activate the polymer portion of the wrapping and/or packaging structure 100 to begin the oxygen scavenging process. This second exposure, for example, can be handled in a UV opaque container that one inserts at least a portion of the wrapped and/or packaged object or product. A UV energy source in the container can be used to activate the oxygen scavenging properties of the polymer.

Alternatively, the polymer film can be arranged as a separate sheet that is separately activated with UV energy and inserted in proximity to, and optionally interposed between, a portion of the object or product and the wrapping and/or packaging structure 100. In this way, the sanitizing agent comprising ozone gas sanitizes the wrapped and/or packaged object or product and then the polymer film substantially scavenges the remaining oxygen from the wrapped and/or packaged object or product.

Note that the term object is used broadly with respect to the present invention. An object as contemplated herein, for example, can represent any product, object, instrument, human or animal anatomy, or any portions thereof, and regardless of whether in solid, fluid, gel, or any other state, as dictated by a particular application in accordance with the present invention.

As shown in FIG. 11, an ultraviolet wand or bar 1102 can serve as an energizing and activating source for converting the oxygen gas to ozone gas contained in the at least one store 106. For example, a sheet dispensing operation, prior to using such sheet 1100 as a sanitizing wrap and/or sanitizing packaging structure 100, includes an energizing and activation of the sanitizing agent comprising ozone gas contained in the sheet.

Before using the wrapping and/or packaging structure 100 for sanitizing an object, the wrapping and/or packaging structure 100 preferably contains in the at least one store 106 a gas atmosphere comprising a relatively high concentration of oxygen gas and a relatively minimal or no significant presence of nitrogen gas therein. Optionally, a mixture of carbon dioxide gas can be included with the oxygen in the atmosphere in the at least one store 106 to help fill the at least one store 106 while allowing a selectable concentration of pure oxygen gas in the mix. Accordingly, before, or during, using the wrapping and/or packaging structure in a sanitizing application, preferably an ultraviolet energy source, such as the UV bar 1102 shown in FIG. 11 or optionally a flat UV panel (not shown), can be used to energize and convert the oxygen gas in the wrapping and/or packaging structure 100 to ozone gas. In this way, at least in part a sanitizing agent comprising ozone gas is contained in the at least one store 106. As an example illustrated in FIG. 11, the ultraviolet light wand or bar 1102 preferably includes a guide channel 1104 whereby the sheet 1100 of packaging and/or wrapping material can be inserted (as shown by directional arrows 1106) and exposed to the ultraviolet light source (in the UV wand or bar) across a substantial portion of the surface of the wrapping and/or packaging structure 100.

In one example, the wrapping and/or packaging material can be slid across the channel 1104 in the ultraviolet light bar 1102 to provide the ultraviolet radiation across the length of a sheet 1100 of the wrapping and/or packaging structure 100. The ultraviolet bar or wand, in this example, is located in close proximity to the surface of the wrapping and/or packaging structure 100 to deliver the ultraviolet energy thereto. Optionally, a reflective surface on one side of the length of the channel 1104 in the ultraviolet light bar 1102 allows reflection of ultraviolet light thereby permitting the ultraviolet light bar to utilize a single source of ultraviolet light on one side of the guide to energize from multiple directions to cover the opposing sides of the sheet with UV energy. That is, the UV energy passes from one side and then passes through the UV transparent packaging and/or wrapping material and then any ultraviolet light that passes through the material is reflected back through the material towards the UV source. In this way, the ultraviolet radiation is provided to opposing surfaces of the sheet 1100 comprising a wrapping and/or packaging structure 100 while the sheet 1100 is sliding through the guide 1104 in the ultraviolet light bar 1102. Alternatively, two sources of ultraviolet light can be located on opposing sides of the guide thereby providing ultraviolet radiation from a source at each surface on top and bottom of the sheet 1100 of the wrapping and/or packaging structure 100. In view of the discussion above, other arrangements of the ultraviolet energy source(s) and/or reflective surfaces to help enhance the amount of ultraviolet radiation transferred to the wrapping and/or packaging structure 100 to activate and convert the oxygen to ozone are anticipated within the scope of the present invention.

The UV source can be provided in other shapes and arrangements for use in different applications for energizing and activating a sanitizing agent comprising ozone gas. For example, a flat panel UV source can cover and energize at least one store 106 in a rectangular area on a sheet. This flat panel UV source arrangement can energize larger sheet areas than the UV bar discussed above. As a second example, the UV source can be located within a container to energize the inside of the container, such as within a box, bottle, or can. In this way, the UV source activates sanitizing agent within the at least one store 106 in the wrapping and/or packaging structure 100 located in the container. Other UV source shapes, arrangements, and configurations can be readily anticipated by one of ordinary skill in the art for use in different packaging applications in accordance with the present invention.

Figure 12:
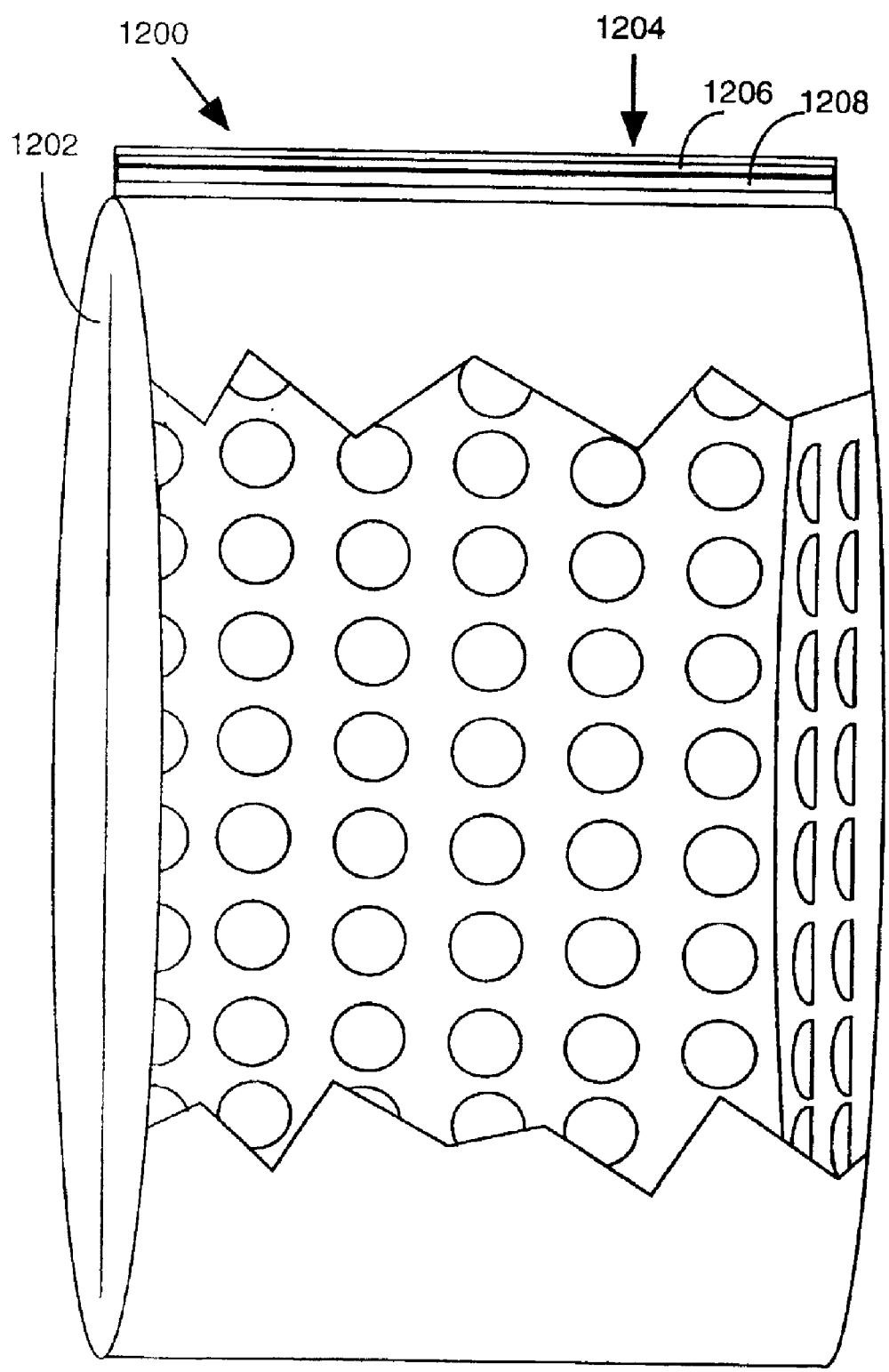
FIG. 12 is a front cut-away view illustrating an exemplary sanitizing bag packaging application in accordance with a preferred embodiment of the present invention.
Figure 13:
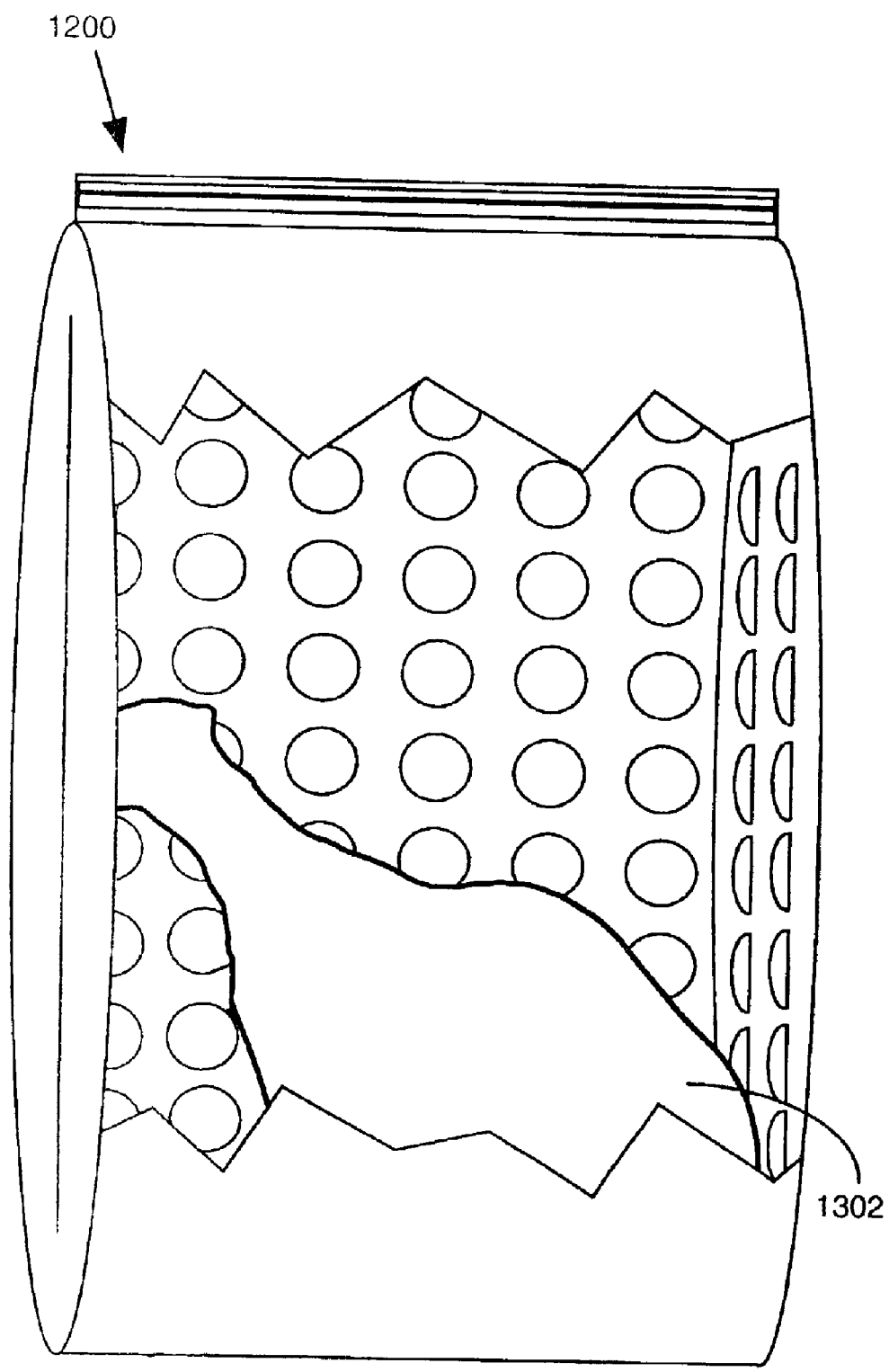
FIG. 13 is a front cut-away view showing a food product being sanitized in the bag of FIG. 12 according to a preferred embodiment of the present invention.

In an alternative embodiment of the present invention, the packaging material is arranged in the form of a bag, as illustrated in FIGS. 12 and 13. The exemplary bag 1200 shown in FIG. 12 comprises a foldable bag 1200 which includes side pleats 1202 to allow flat folding the bag 1200 for easy and convenient storage. The bag 1200 also includes, according to a preferred embodiment, an opening 1204 at one end for receiving an object or a product within the bag 1200. This 1204 opening preferably includes a re-sealable locking channel 1206 and mating tab 1208 structure to allow the bag 1200 to be sealed by mating the tab structure with the channel structure at the opening 1204 of the bag. In this way, the bag 1200 can be stored relatively flat with the sealed opening maintaining the inner portion of the bag in a sealed and sanitary enclosure until ready to be used. When the bag is ready to be used, the tab and channel structures can be pulled apart to open the bag and then an object or a product, such as a food product or a medical instrument, can be stored in the inner portion of the bag and then the opening can be re-sealed by re-mating the tab and channel structures together. See for example FIG. 13 with a food product 1302 shown stored in the bag 1200.

As shown in FIG. 13, a food product, such as a piece of poultry 1302, is stored and packaged in the bag 1200 thereby receiving the beneficial sanitizing effect of the sanitizing agent comprising ozone gas being transferred from the at least one store 106 in the bag 1200. The piece of poultry 1302 is stored or packaged conveniently and sanitized in the bag 1200 for enhancing the sanitary and hygienic conditions of the piece of poultry 1302 for an extended period of time. The sealed bag 1200 provides a barrier against external contaminants thereby prolonging the beneficial sanitizing effect. In this way, the sanitizing packaging can be conveniently stored and used to sanitize and/or reduce microorganisms from the food product stored in the bag 1200.

Accordingly, in the stored condition, prior to use, the bag 1200 comprises at least one store 106 that preferably contains a gas mixture comprising a high concentration of pure oxygen and optionally a portion of carbon dioxide gas with minimal or no presence of nitrogen gas. Additionally, the inner portions of the bag preferably contain a sealed environment that optionally comprises a high concentration of carbon dioxide gas to maintain a minimal atmosphere therein. However, the minimal atmosphere preferably comprises no amount of nitrogen gas.

When ready to use, the bag can be subjected to an ultraviolet energy source providing energy through the outer gas impermeable (or low gas permeable) layer of the bag through to the stores containing the high concentration of oxygen gas. An ultraviolet energy source, such as discussed before, would radiate through the bag 1200. The first layer 102 and second layer 104,702, which may include micro-perforations 704, in one alternative embodiment, would be transparent to the UV energy allowing energizing the inner portions of the sealed bag 1200 and the stores 106 contained therein. In this way, an ultraviolet energy source can radiate through the bag 1200 and energize and activate the oxygen gas contained in the at least one store 106 in the bag 1200 and convert the oxygen gas to a high concentration of pure ozone. Because there is minimal or no concentration of nitrogen gas in the bag there will be no undesirable byproduct gases and/or chemicals in the bag. After the bag has been energized and the pure oxygen is substantially converted to pure ozone in the bag in the stores, the bag is ready to be used to store and package an object or a product for sanitizing the product therein. The bag can be opened, by pulling apart the channel structure 1206 from the tab structure 1208 about the opening 1204, and then inserting the object or product to be sanitized, such as the piece of poultry 1302, in the bag 1200.

Further, the micro-perforations 704 and/or permeability of the second layer 104,702, can be selectively located over portions of the inner bag structure to enhance the transfer rate of the sanitizing agent comprising ozone gas in certain portions of the inner bag, while providing a selected slower transfer rate over other portions of the inner bag. This selective fast and slow transfer rate provided over different stores 106, for example, can provide a rapid transfer of sanitizing agent comprising ozone gas to provide immediate beneficial sanitizing effect to a product in the bag while additionally providing an extended sanitizing effect to the food product over a longer period of time. Ozone gas normally has a relatively short period of time for sanitizing an object or product once exposed to and contacting the surface of an object or product before the ozone converts to oxygen and mixes with any fluids of the object or product. Therefore, for example, by staggering the selected transfer rate of proximate stores 106 in the bag structure, the bag can provide both an immediate beneficial sanitizing effect and a continuous extended sanitizing effect over the entire surface area of the inner bag structure such as to enhance a wrapped or packaged product's shelf life.

While the bag has remained sealed, the stores 106 have contained the high concentration of oxygen gas. The inner compartment of the bag 1200 preferably has substantially remained in an atmosphere comprising a high concentration of carbon dioxide. After the UV energy source radiates through the bag 1200, the oxygen is substantially converted to ozone gas, and the sanitizing agent comprising ozone gas is ready to be used on the object or product.

Additionally, opposing surfaces of the portions of the second layer 104,702, within the bag help to provide a retaining and capturing effect for the stores 106 to retain the gas atmosphere comprising a high concentration of pure oxygen. The opposing portions of the second layer 104,702 tend to contact at the surfaces or remain in close proximity to each other thereby providing sealing pressure to contain the gas atmosphere within the stores 106 until ready to be used.

When the bag 1200 is opened the second layer 104,702 begins to allow transfer of the sanitizing agent comprising ozone gas from the stores into the main compartment of the bag. This transfer rate is not instantaneous. It is a gradual process that allows ample time for inserting an object or a product in the bag 1200 and then closing or sealing the bag 1200 about a closure structure about the opening, such as discussed above, to maintain the product and/or object sealed within the bag 1200 while providing the beneficial sanitizing effect to the surfaces of the object.

Furthermore, the stores 106 in the inner bag structure can be selectively released for use in a sanitizing application such that the bag can be reused to provide sanitizing benefit to a product over a number of subsequent uses. For example, a plurality of strippable layer strips 108 (such as illustrated in FIG. 1) can be selectively covering certain stores 106 in a bag 1200. For each sanitizing application of the bag 1200, a user can selectively remove at least one of the plurality of strippable layer strips 108 to activate and release the sanitizing agent comprising ozone gas contained in the stores 106 covered by the removed at least one of the plurality of strippable layer strips 108.

In one preferred alternative embodiment, a plurality of strips 108 are arranged about the inner bag with one or more strips 108 in association, such as indicated by a common attribute such as a common colorization treatment to indicate the association. The at least one strip 108, as indicated such as by a common color of the at least one strip 108, is then removed by a user of the bag to re-use the bag in a sanitizing re-application by activating and releasing a plurality of stores 106 covered by the at least one strip 108. For a subsequent sanitizing application (re-use of the bag), for example, the user would remove a second at least one strip 108 of a different common color. For example, a blue colored association of strips 108 would be removed for a first sanitizing application of the bag, and then a yellow colored association of strips 108 would be removed by the user for a second sanitizing application (re-use of the bag). As can be appreciated by those skilled in the art, other attributes of the association of the at least one strip 108 can be used to indicate grouping for common release in sanitizing applications and re-use of the sanitizing bag. For example, patterns and/or colors on or about an association of strips 108 can be used as indicators of a common use for a sanitizing application. Also, shapes of the at least one strip can be used to indicate a common grouping for a common use in a sanitizing application of the bag.

Note that any stores 106 that are not used at any particular sanitizing application of the bag will normally continue to contain the sanitizing agent comprising ozone gas. The ozone gas eventually converts back to pure oxygen gas and continues to be contained in the at least one store 106 until a later activation and energizing step, such as by re-exposure to UV energy. In this way, the stores 106 can be selectively released for use in sanitizing applications. Stores that are not released for use at a particular use of the bag will also be activated, such as by exposure to UV energy, and will temporarily contain the sanitizing agent comprising ozone gas. But, the ozone gas in these unused stores 106 will convert back to oxygen and will be ready for future activation and use in a later application of and re-use of the bag 1200. This provides a significant advantage, in accordance with the present invention, allowing re-usability of the sanitizing bag 1200 for repeated sanitizing applications to objects or products. Alternative means of releasing the stores 106 for subsequent re-use of the bag 1200 can be readily anticipated by those of ordinary skill in the art. For example, alternative mechanical release barrier mechanisms can provide selective release of stores 106 for subsequent transfer of sanitizing agent comprising ozone gas to objects or products in the re-usable bag 1200.

Figure 14:
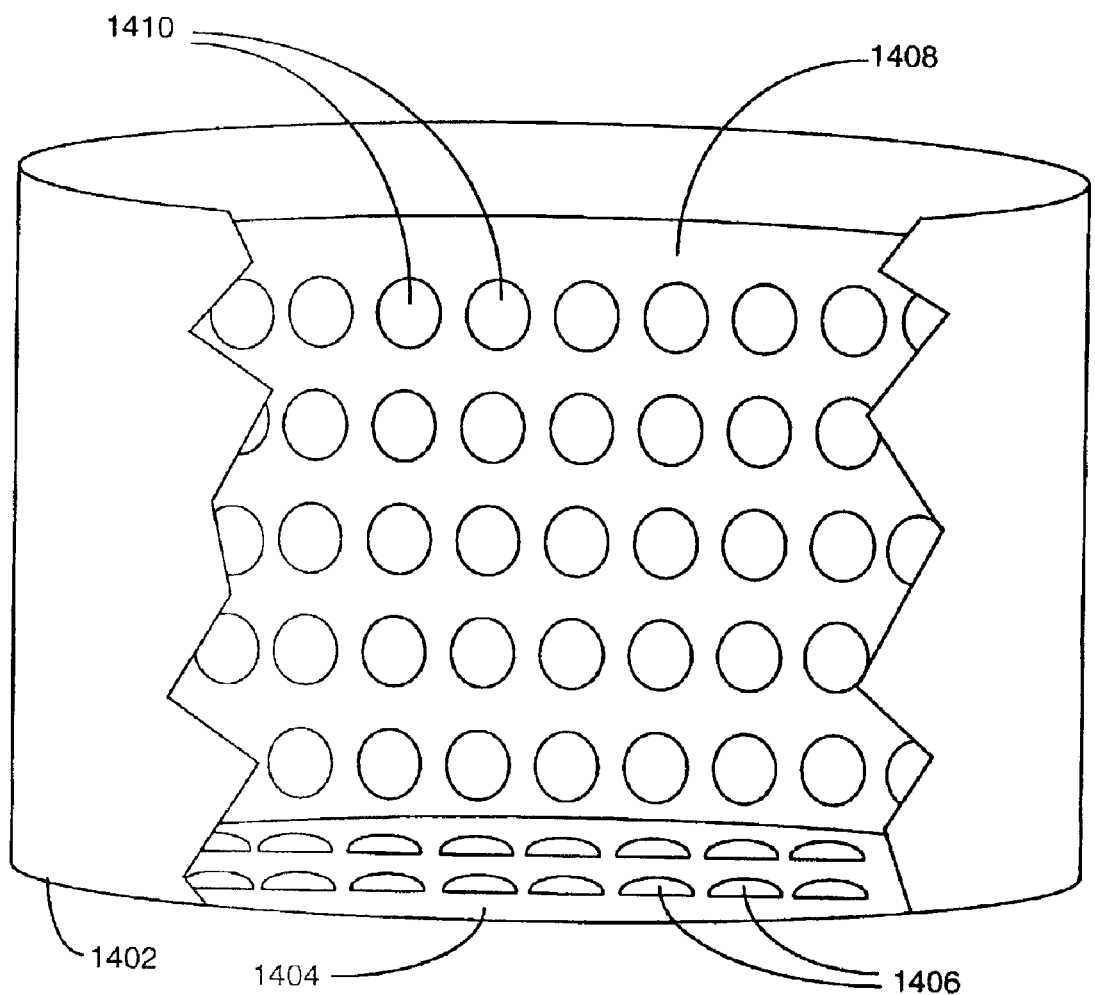
FIGS. 14 and 15 are front cut-away views illustrating two exemplary rigid structure sanitizing packaging applications according to alternative preferred embodiments of the present invention.
Figure 15:
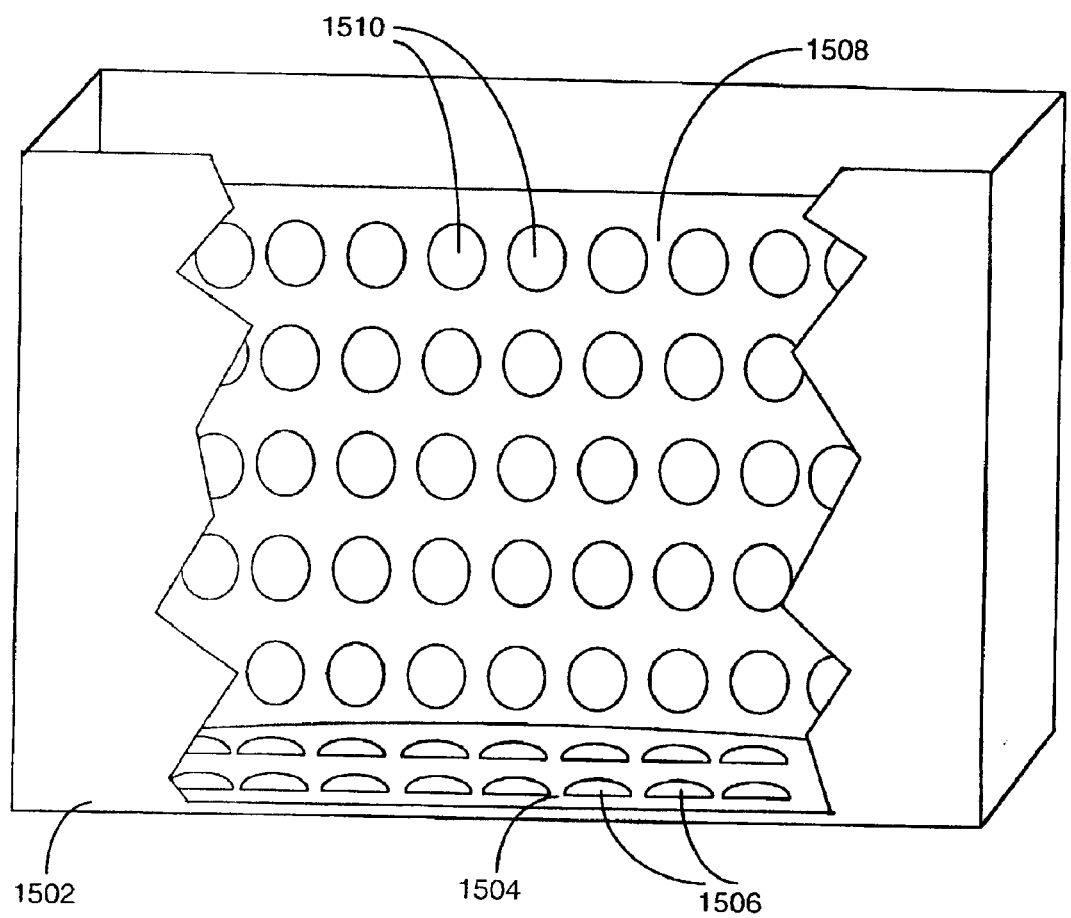

In another exemplary alternative embodiment of the present invention, a relatively rigid structure such as a box 1502, or, such as a bottle, a can, and a cylinder 1402, can provide sanitizing effect to products or objects that are packaged any such container, as illustrated in FIGS. 14 and 15. A liner 1404,1408, or 1504, 1508, can be formed within the package of the rigid structure including the first gas impermeable (or low gas permeable) layer 102 and a second optionally gas permeable layer 104,702, (preferably including micro-perforations 704), containing at least one store 106 therebetween. The rigid package, such as a cylinder or box can include a liner film or sheet structure comprising the at least one store 106, also indicated by drawing elements 1406,1410, and drawing elements 1506,1510, to provide sanitizing effect to an object or product stored in the rigid package when in use. The at least one store 106 can contain a gas atmosphere comprising a high concentration of pure oxygen gas and optionally carbon dioxide gas to maintain a selected mixture of pure oxygen in the atmosphere within each of the at least one store 106. The rigid structure preferably comprises an opening portion to allow an object or a product to be inserted and removed from the rigid packaging structure.

About the opening of the rigid package, such as a box, canister, or tumbler, includes a cap, lid, or other closure structure (not shown) that can form a seal to maintain the inner portion of the rigid structure in a sealed enclosure. Preferably, the rigid structure is maintained sealed with the cap or lid until ready to be used, where the inner portion of the rigid structure preferably contains an atmosphere comprising a high concentration of carbon dioxide gas and minimal or no significant concentration of nitrogen gas. In one exemplary preferred embodiment, the second layer includes micro-perforations to allow transfer of the sanitizing agent comprising ozone gas. The inner gas pressure in the closed container is mechanically coupled to the at least one store 106 and tends to provide a removable barrier thereto by gas pressure about the micro-perforations to help reduce transfer of the oxygen gas atmosphere and/or sanitizing agent comprising ozone gas via the micro-perforations of the at least one store 106 until ready to use the package. In this way, the liner comprising the at least one store 106 can continue to retain and capture the gas atmosphere comprising the high concentration of pure oxygen within the at least one store 106 until ready to be used, such as when the container is opened to insert an object or product.

When ready to use the rigid container, the inner portion of the rigid container and the liner, 1404,1408, or 1504,1508, are preferably exposed to an ultraviolet radiation energy source to energize and activate the pure oxygen gas within the at least one store 106 and convert the pure oxygen to a high concentration of pure ozone within the at least one store 106. If the outer rigid structure of the rigid container is transparent, or relatively transparent to the ultraviolet light radiation energy, the ultraviolet source can be located outside of the rigid container and transmit the energy through the outer rigid structure of the container to energize and convert the oxygen within the at least one store 106 to the high concentration of pure ozone. Alternatively, if the rigid structure is opaque or not sufficiently transparent to ultraviolet light radiation energy, then the lid or cap or top structure can be removed from the opening of the rigid container and an ultraviolet light energy source can be delivered through the opening of the container to expose the liner, 1404,1408, or 1504,1508, and inner portions of the container to the ultraviolet light radiation energy thereby converting the pure oxygen to pure ozone when ready to be used for providing the beneficial sanitizing effect.

After the lid or top of the container is removed and the at least one store 106 contains and begins to transfer a sanitizing agent comprising a high concentration of pure ozone, an object or a product can be inserted into the rigid structure container to store within the container while providing the beneficial sanitizing effect to the object and/or product. After the object or product has been inserted into the rigid container, the lid and/or cap can be replaced over the opening to seal the object and/or product within the rigid container thereby prolonging the beneficial sanitizing effect to the object and/or product sealed within the rigid container.

Additionally, in an alternative embodiment of the present invention, the lid and/or cap can also contain a liner portion on the inner side of the lid and/or cap which can be exposed to the ultraviolet light energy radiation before, or during, use in a sanitizing containing application. In this way, an object and/or product that is stored within the rigid container, including the cap and/or lid providing the seal over the opening of the container, receives the beneficial sanitizing effect from all directions and all exposed surfaces to the inner liner portion of the rigid container.

Further, the micro-perforations 704 and/or permeability of the second layer 104,702, can be selectively located over portions of the inner liner structure to enhance the transfer rate of the sanitizing agent comprising ozone gas in certain portions of the inner liner, while providing a selected slower transfer rate over other portions of the inner liner. This selective fast and slow transfer rate provided over different stores 106, for example, can provide a rapid transfer of sanitizing agent comprising ozone gas to provide immediate beneficial sanitizing effect to a product in the rigid container while additionally providing an extended sanitizing effect to the food product over a longer period of time. Ozone gas normally has a relatively short period of time for sanitizing an object or product once exposed to and contacting the surface of the object or product before the ozone converts to oxygen and mixes with any fluids of the object or product. Therefore, for example, by staggering the selected transfer rate of proximate stores 106 in the liner structure, the rigid container can provide both an immediate beneficial sanitizing effect and a continuous extended sanitizing effect over the entire surface area of the inner liner structure such as to enhance a packaged product's shelf life.

Furthermore, the stores 106 in the liner structure can be selectively released for use in a sanitizing application such that the rigid container can be reused to provide sanitizing benefit to a product over a number of subsequent uses. For example, a plurality of strippable layer strips 108 (such as illustrated in FIG. 1) can be selectively covering certain stores 106 in a container. For each sanitizing application of the container, a user can selectively remove at least one of the plurality of strippable layer strips 108 to activate and release the sanitizing agent comprising ozone gas contained in the stores 106 covered by the removed at least one of the plurality of strippable layer strips 108. Note that any stores 106 that are not used at any particular application of the container will normally continue to contain the sanitizing agent comprising ozone gas. The ozone gas eventually converts back to pure oxygen gas and continues to be contained in the at least one store 106 until a later activation and energizing step, such as by re-exposure to UV energy. In this way, the stores 106 can be selectively released for use in sanitizing applications. Stores that are not released for use at a particular use of the container will also be activated, such as by exposure to UV energy, and will temporarily contain the sanitizing agent comprising ozone gas. But, the ozone gas in these unused stores 106 will convert back to oxygen and will be ready for future activation and use in a later application of and re-use of the rigid container. This provides a significant advantage, in accordance with the present invention, allowing re-usability of the sanitizing container for repeated sanitizing applications to objects or products. Alternative means of releasing the stores 106 for subsequent re-use of the rigid container can be readily anticipated by those of ordinary skill in the art. For example, alternative mechanical release barrier mechanisms can provide selective release of stores 106 for subsequent transfer of sanitizing agent comprising ozone gas to objects or products in the re-usable rigid container.

In one preferred alternative embodiment, a plurality of strips 108 are arranged about the inner lining with one or more strips 108 in association, such as indicated by a common attribute such as a common colorization treatment to indicate the association. The at least one strip 108, as indicated such as by a common color of the at least one strip 108, is then removed by a user of the sanitizing container to re-use the container in a sanitizing re-application by activating and releasing a plurality of stores 106 covered by the at least one strip 108. For a subsequent sanitizing application (re-use of the container), for example, the user would remove a second at least one strip 108 of a different color. For example, a blue colored association of strips 108 would be removed for a first sanitizing application of the container, and then a yellow colored association of strips 108 would be removed by the user for a second sanitizing application (re-use of the container). As can be appreciated by those skilled in the art, other attributes of the association of the at least one strip 108 can be used to indicate grouping for common release in sanitizing applications and re-use of the sanitizing container. For example, patterns and/or colors on or about an association of strips 108 can be used as indicators of a common use for a sanitizing application. Also, shapes of the at least one strip can be used to indicate a common grouping for a common use in a sanitizing application of the container.

Figure 17:
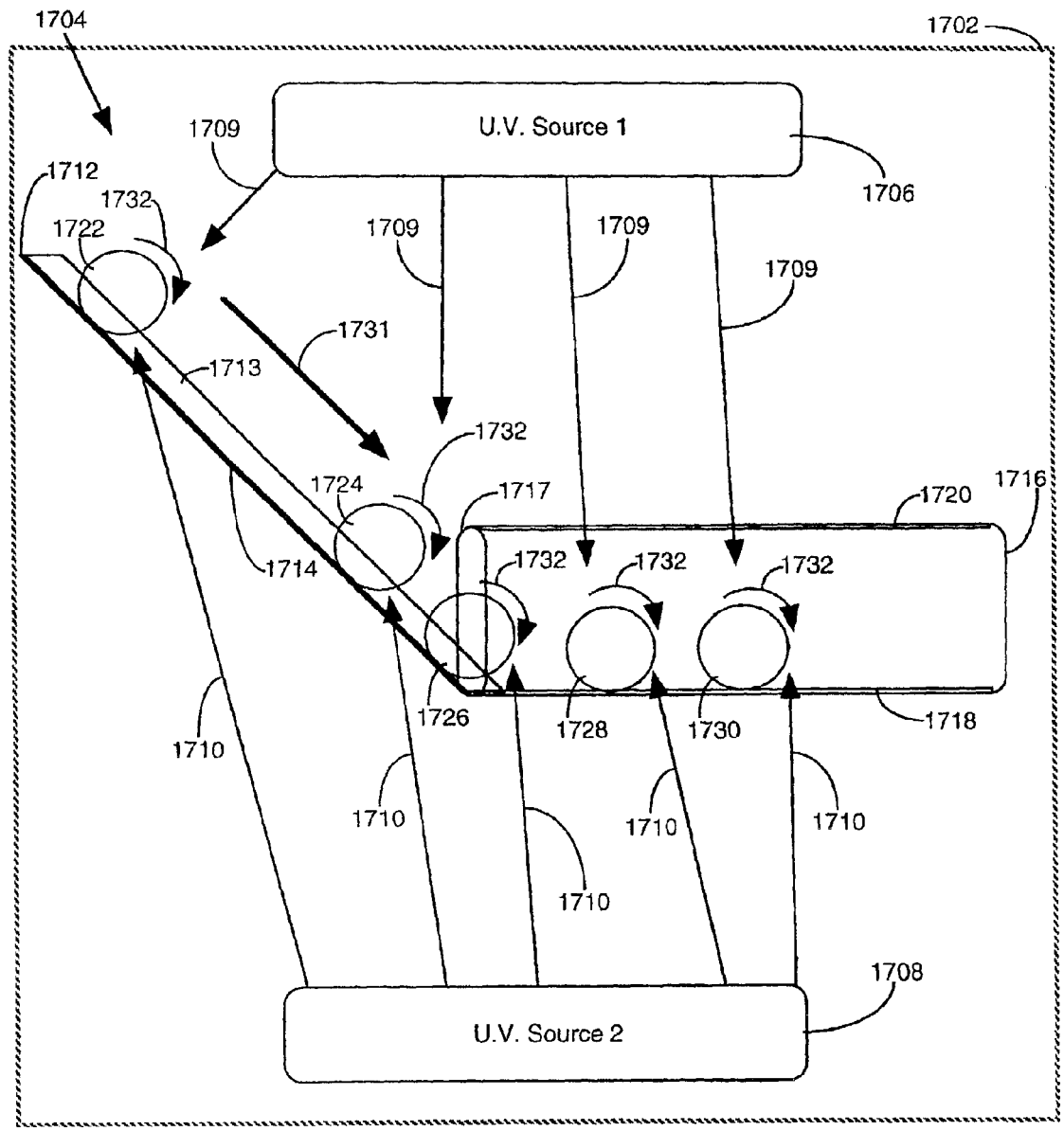
FIG. 17 is a side view of an exemplary packaging system according to a preferred embodiment of the present invention.
Figure 18:
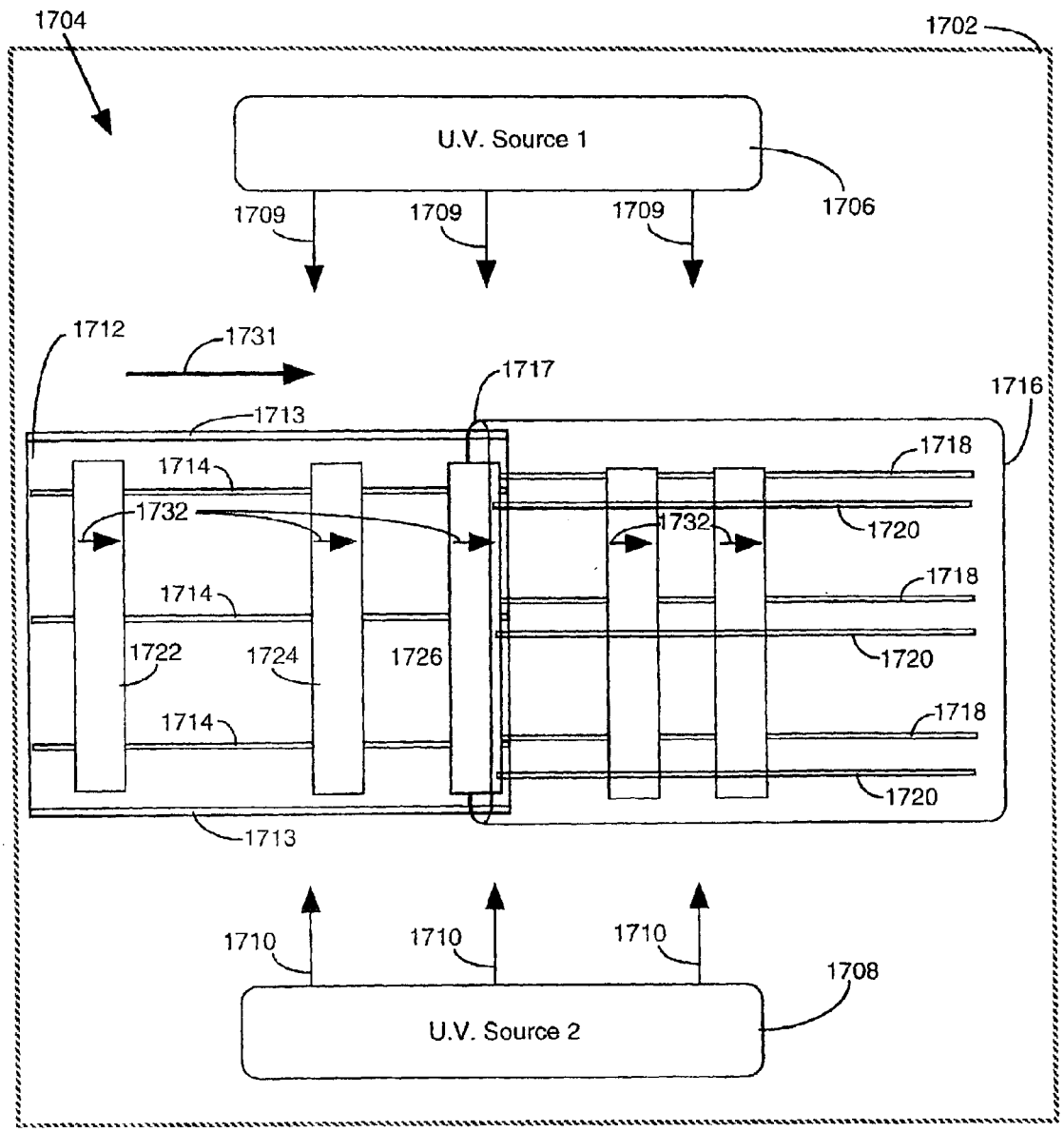
FIG. 18 is a top view of the exemplary packaging system shown in FIG. 17.

Referring to FIGS. 17 and 18, an exemplary system for providing a sanitizing, disinfecting, and/or sterilizing treatment to products and/or objects being packaged is shown according to a preferred embodiment of the present invention. FIG. 17 shows a side view of the system while FIG. 18 shows a top view of the system. Preferably, the system operates in a substantially contained environment 1702, or at least a partially contained environment. However, in certain applications the system may operate in an open uncontained environment. The environment 1702 will typically include an atmosphere 1704 that comprises a sanitizing agent comprising ozone. However, at times the atmosphere 1704 may contain a convertible agent that can be converted to a sanitizing agent comprising ozone, such as by exposure to ultraviolet energy. A first U.V.Source 1706 that radiates 1709 U.V. energy within the environment where the system is operating. Additionally, a second U.V. source 1708 may also be radiating 1710 U.V. energy in the environment that includes the system. The operational system includes an inclined chute 1712 that guides product into the opening 1717 of a receiving packaging 1716, such as a bag or other container. The incline or chute 1712 preferably includes guard walls 1713 on either side of the incline or chute 1712 to help guide product down the chute 1712 and into the bag or container 1716. The product or objects move down 1731 guided by the chute 1712 and into the opening 1717 of the packaging or container 1716, such as a bag. Five objects or products 1722, 1724, 1726, 1728, 1730, are illustrated moving down 1731 the chute 1712 and into the container packaging 1716. The ultraviolet radiation from the first U.V. Source 1706 and the second U.V. Source 1708 can penetrate and deliver the U.V. energy through the structure of the guiding incline or chute 1712 as well as through the container or packaging 1716 to directly expose all of the environment 1702 with the ultraviolet energy. This helps to energizably convert the convertible agent to the sanitizing agent comprising ozone, under a first ultraviolet radiation energy, and further can help to convert the sanitizing agent comprising ozone to the convertible agent, under a second ultraviolet energy, as will be discussed in more detail below. Further, as the products or objects 1722, 1724, 1726, 1728, 1730, are being guided down 1731 from the inclined chute 1712 into the opening 1717 of the bag or container or packaging 1716 the surfaces of the products or objects 1722, 1724, 1726, 1728,1730 will be more fully exposed to the ultraviolet radiation energy from the first U.V. Source 1706 and the second U.V. Source 1708. Optionally, the bottom surface 1714 of the incline or chute 1712 can be provided with a rough surface, or ridges, that can at least partly grip the surface of the products or objects moving down 1731 the inclined chute 1712 to thereby introduce a rotational motion 1732 to the products and/or objects 1722, 1724, 1726, 1728, 1730. This rotational motion 1732 helps to further expose to the ultraviolet radiation and to the sanitizing agent comprising ozone to all of the surfaces of the products or objects 1722, 1724, 1726, 1728, 1730 being guided into the container 1716 for packaging. Additionally, a rough surface or ridges 1718, 1720, can be added to the container or bag 1716 for additionally providing the rotational motion 1732 to the objects or products 1722, 1724, 1726, 1728, 1730, being introduced into the container and packaging 1716. Preferably, the rough surfaces, or ridges 1714, 1718, 1720, are transparent to the ultraviolet energy radiation from the first U.V. Source 1706 and the second U.V. Source 1708. This allows the ultraviolet energy radiation to penetrate through these rough surfaces, or ridges structures 1714, 1718, 1720. According to a preferred embodiment, the rough surfaces, or ridges, 1714, 1718, 1720, are provided as strips along the length of the inclined chute 1712 and the length of the bottom surface and top surface of the container or bag 1716 for packaging. Note that by adding the strips to the top and bottom of the container or bag 1716 it is a symmetrical arrangement such that the bag can be located either way with respect to the incline 1712 to receive the products or objects 1722, 1724, 1726, 1728, 1730. This makes the product or object packaging operation much simpler and efficient.

According to a preferred embodiment of the present invention, the product or objects 1722, 1724, 1726, 1728, 1730, may comprise hot dogs that are being packaged such as in a container or bag 1716. However, those of ordinary skill in the art may appreciate that other objects or product may likewise be substituted for the hot dogs where these objects or products are to be bulk loaded into the container and/or bag 1716 for packaging. Notice that the packaging operation allows the contained, or partially contained environment or atmosphere within the container or bag 1716 to receive the ultraviolet radiation from the first U.V. Source 1706 and the second U.V. Source 1708. While the hot dog products 1722, 1724, 1726, 1728, 1730, are rotationally introduced into the container and/or bag 1716 for packaging the atmosphere in the container or bag 1716 can be energized the ultraviolet radiation. According to a first ultraviolet radiation from the first U.V. Source 1706 and the second U.V. Source 1708, such as about a substantially 253 nm wavelength range for the ultraviolet radiation energy, a strong anti-microbial killing treatment of ultraviolet radiation energy is applied to the hot dog products 1722, 1724, 1726, 1728, 1730, being packaged in the container and/or bag 1716. This frequency of ultraviolet radiation energy, besides having the anti-microbial killing effect directly on the surfaces and the atmosphere in the container and bag 1716, also has the effect of converting sanitizing agent comprising ozone back to a convertible agent such as air with oxygen. Hence, for a period of time while the ultraviolet energy radiation is radiated in the environment 1702 at a first frequency such as about 253 nm wavelength range for ultraviolet radiation energy, the surfaces within the environment 1702, such as all the exposed surfaces of the hot dog products 1722, 1724, 1726, 1728, 1730, and the surfaces of the container and bag 1716, and the inclined chute surfaces 1712 will be exposed to the strong anti-microbial killing ultraviolet energy.

At a second timed interval, the ultraviolet energy radiated from the first U.V. Source 1706 and the second U.V. Source 1708 comprises ultraviolet radiation energy that is substantially a frequency of about 185 nm wavelength range. This radiation 1709, 1710, will energize the convertible agent comprising oxygen and convert it to the sanitizing agent comprising ozone. This conversion takes place within the environment 1702 and including within the container and/or bag 1716 that is packaging the hot dog products 1722, 1724, 1726, 1728, 1730. The sanitizing agent comprising ozone has a strong lingering effect for killing microbes that may be resident on the exposed surfaces as on the hot dog products 1722, 1724, 1726, 1728, 1730, and the exposed surfaces of the inclined chute 1712 and the container and/or bag 1716. The sanitizing agent comprising ozone provides additional sanitizing and/or sterilizing effect to the packaged hot dog products 1722, 1724, 1726, 1728, 1730 in the container and/or bag 1716. Once the container and/or bag 1716 is filled with the desired amount of product 1722, 1724, 1726, 1728, 1730, then the opening 1717 can be sealed and the packaged hot dog products 1722, 1724, 1726, 1728, 1730, can be delivered from the packaging operation to a post-processing station. During the delivery the container and/or bag 1716 contains an atmosphere and environment that can be additionally treated by ultraviolet radiation energy to alternatively provide the anti-microbial killing ultraviolet energy frequency to the surfaces exposed within the container and/or bag 1716 while converting any sanitizing agent comprising ozone in the container and/or bag 1716 back to the convertible agent comprising oxygen. Then at a second ultraviolet energy frequency the convertible agent comprising oxygen in the container and/or bag 1716 can be converted to the sanitizing agent comprising ozone to provide additional sanitizing and/or sterilizing treatment to the packaged products 1722, 1724, 1726, 1728, 1730. This dual action treatment provides significant sanitizing and/or sterilizing effect to the packaged hot dog products 1722, 1724, 1726, 1728, 1730, that will then remain packaged in the sealed container and/or packaging 1716 until ready to be consumed by the user. Advantageously, all surfaces of the products and/or objects will be exposed to both the ultraviolet energy with anti-microbial killing effect and further to the sanitizing agent comprising ozone that provides additional long term sanitizing and/or sterilizing effect to the products in the package 1716. Note that this treatment can be applied to other products and/or objects being packaged such as in the medical field instrumentation that needs to be guided into packaging may benefit from this system as discussed with reference to FIGS. 17 and 18.

Figure 19:
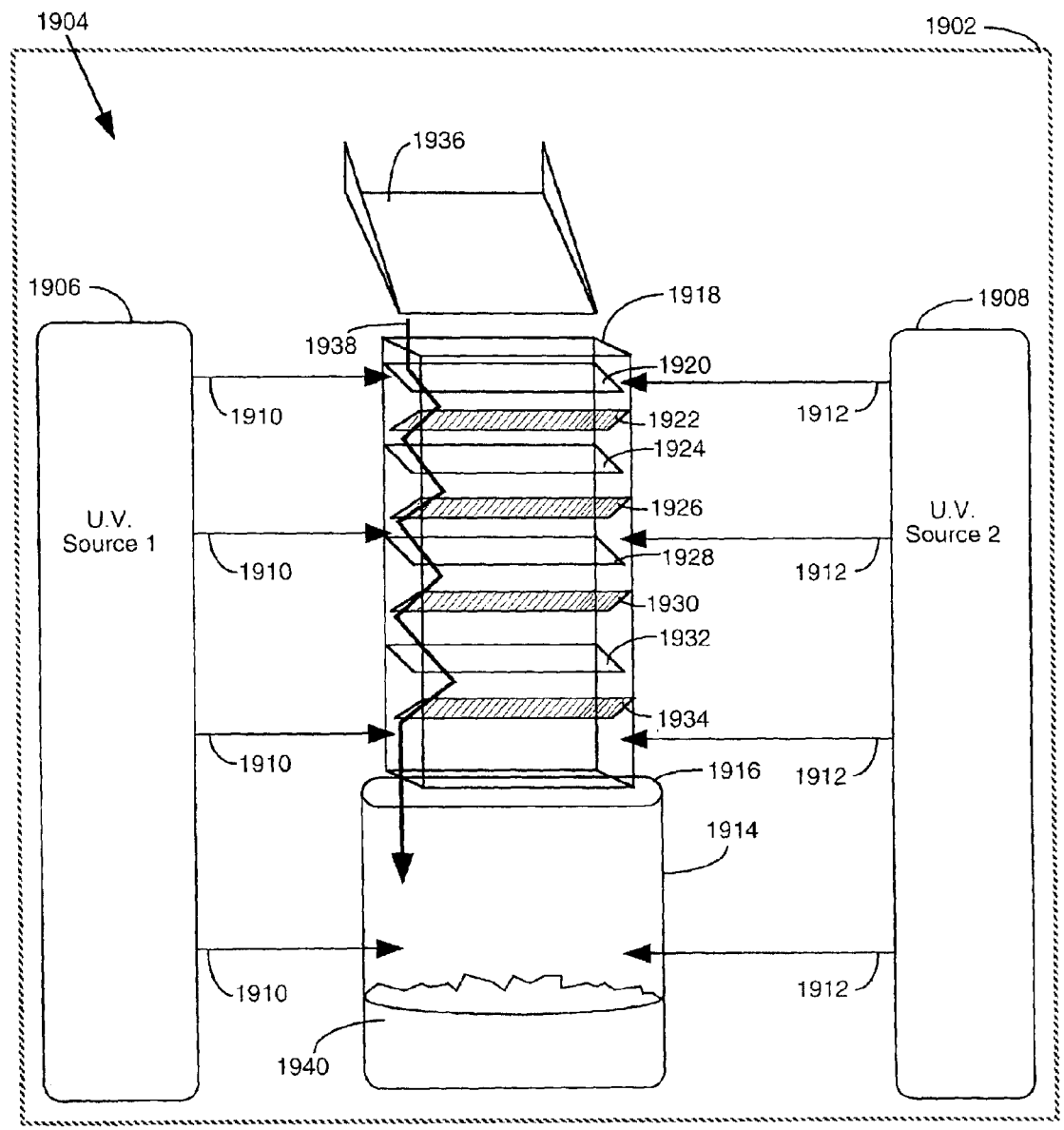
FIG. 19 is a side view of another exemplary packaging system according to an alternative preferred embodiment of the present invention.

Referring to FIG. 19, an alternative preferred embodiment for packaging product or objects is shown. The system for packaging objects or products is preferably contained in an environment 1902 comprises an atmosphere 1904. The environment 1902, alternatively, can be partially contained or even in open area while operating the system for packaging the products and/or objects. The atmosphere 1904 can contain a sanitizing agent comprising ozone. A first U.V. Source 1906 radiates 1910 U.V. energy into the environment 1902. A second U.V. Source 1908 also radiates 1912 U.V. energy into the environment 1902. Although two U.V. energy sources 1906, 1908 are illustrated in this example, a system may operate with at least one U.V. energy source 1906 or 1908 for providing U.V. energy into the environment 1902. A container and/or bag 1914 receives the products and/or objects 1940 that are being packaged in the container and/or bag 1914. An opening 1916 in the container and/or bag 1914 receives the products and/or objects being packaged. The products and/or objects are delivered via an inclined chute 1936 that guides the products and/or objects into a baffle structure 1918 that guides products and/or objects into the opening 1916 of the container and/or bag 1914 while providing a rotational, and/or a mixing, motion to the products and/or objects being guided through the baffle structure 1918 and into the container and/or bag 1914. The baffle structure 1918 includes a series of inclined shelves 1920, 1922, 1924, 1926, 1928, 1930, 1932, 1934, that are arranged in alternatively opposing inclined fashion such that the products and/or objects that fall through the baffle structure 1918 will follow a path such as shown by the arrow 1938 and thereby obtain rotational motion while passing over the opposing inclined shelves 1920, 1922, 1924, 1926, 1928, 1930, 1932, 1934. The baffle structure 1918 is preferably comprising material that is substantially transparent to the ultraviolet radiation energy that is radiated in 1910 from the first ultraviolet energy source 1906 and radiated 1912 from the second ultraviolet energy source 1908. This allows the ultraviolet radiation energy 1910, 1912, to substantially transfer through the baffle structure 1918 and onto the surfaces and environment within the baffle structure 1918. The products and/or objects being dropped through the baffle structure 1918, therefore, will be substantially exposed to the ultraviolet energy radiation 1910, 1912. Additionally, the atmosphere within the baffle structure 1918 will also be substantially exposed to the ultraviolet radiation energy 1910, 1912. Additionally, the container and/or bag 1914 is also comprising material that is substantially transparent to ultraviolet radiation energy 1910, 1912, thereby allowing the ultraviolet radiation energy 1910, 1912, to enter within the container and/or bag 1914 and radiate onto the surfaces within the container and/or bag 1914 as well as the atmosphere and environment within the container and/or bag 1914. The products and/or objects being delivered into the container and/or bag 1914 through the baffle structure 1918, therefore, will be substantially bathed by the ultraviolet radiation energy 1910, 1912. The rotational, and/or mixing, motion imparted onto the objects and/or products being dropped through the baffle structure 1918 will substantially expose all of the surfaces of the products and/or objects to the ultraviolet radiation energy 1910, 1912. This exposure to the ultraviolet radiation energy 1910, 1912 occurs from the starting point, such as at the guiding incline or chute 1936, which preferably is also made of material that is transparent to ultraviolet radiation energy 1910, 1912, and continues through the baffle structure 1918, and into the container and/or bag 1914 used for packaging the products and/or objects 1940. As should have become obvious to those of ordinary skill in the art other forms of baffle structure 1918 can be utilized in this system to provide the desired rotational, and/or mixing motion to the products and/or objects being delivered into the container and/or bag 1914 through the baffle structure 1918. Similar to the earlier discussion above with respect to FIGS. 17 and 18, the ultraviolet radiation energy 1910, 1912, can be alternatively applied at a first frequency of ultraviolet radiation, such as about 253 nm wavelength range, for providing a strong anti-microbial killing effect on all surfaces in the environment 1902, including the surfaces of the products and/or objects being packaged in the container and/or package material 1914, and alternatively can be exposed to a second ultraviolet radiation energy frequency, such as about 185 nm wavelength range, to convert the convertible agent comprising oxygen to the sanitizing agent comprising ozone. The sanitizing agent comprising ozone provides additional sanitizing and/or sterilizing effect to the products and/or objects being packaged in the container and/or bag 1914. After the container and/or bag 1914 is filled with the desired amount of products and/or objects 1940 the opening 1916 can be sealed to contain within the container and/or bag 1914 the product in an environment that will be protected from external hazards and contaminants while still receiving, as desired, the ultraviolet energy radiation 1910, 1912, to alternatively provide the strong anti-microbial killing effect of the ultraviolet radiation energy at a first frequency, such as about 253 nm wavelength range, and providing the additional sanitizing and/or sterilizing effect of the sanitizing agent comprising ozone being energizeably converted from the convertible agent while being exposed to the ultraviolet radiation energy at the second frequency, such as at about 185 nm wavelength range. The container and/or bag 1914 can then be delivered to a post processing station with the contained products and/or objects being sanitized and/or sterilized as desired by the particular application.

According to another alternative embodiment, the baffle structure 1918 can be included within the package container and/or bag 1914 for transport with the products and/or objects 1940. If the products and/or objects 1940 are packaged in the container and/or bag 1914 with the baffle structure 1918 such that there is sufficient space for movement of the products and/or objects 1940 within the container and/or bag 1914, the sealed container and/or bag 1914 can be provided with alternative inclined action, such as via a conveyer belt system, that will provide additional rotational, and/or mixing, motion to the contained products and/or objects 1940 inside the container and/or bag 1914, while delivering to the post processing station. During this delivery process, further exposure to ultraviolet radiation energy can provide additional sanitizing and/or sterilizing treatment to the contained products and/or objects 1940 in the sealed container and/or bag 1914. The rotational motion while sealed provides exposure of surfaces of the products and/or objects to the ultraviolet radiation energy 1910, 1912, as well as to the sanitizing agent comprising ozone. This enhances the effect for sanitizing or sterilizing the contained products and/or objects 1940. Note that similarly, with reference to FIGS. 17 and 18, the contained products and/or objects 1722, 1724, 1726, 1728, 1730, can rotate on the rough surface 1718, 1720, and thereby expose surfaces to the ultraviolet radiation energy 1709, 1710, and to the sanitizing agent comprising ozone for providing additional sanitizing and/or sterilizing effect to the products and/or objects 1722, 1724, 1726, 1728, 1730, in the sealed container and/or bag 1716 while being delivered to the post processing station. The exemplary system being discussed with reference to FIG. 19, could handle objects and/or products that are not necessarily of a symmetrical dimension that would rotate easily on inclines. For example, products such as seeds and/or spices and/or screws or other hardware that may have odd shapes and that do not easily rotate on an incline would be perfect candidates for such a baffle structure 1918.

Figure 20:
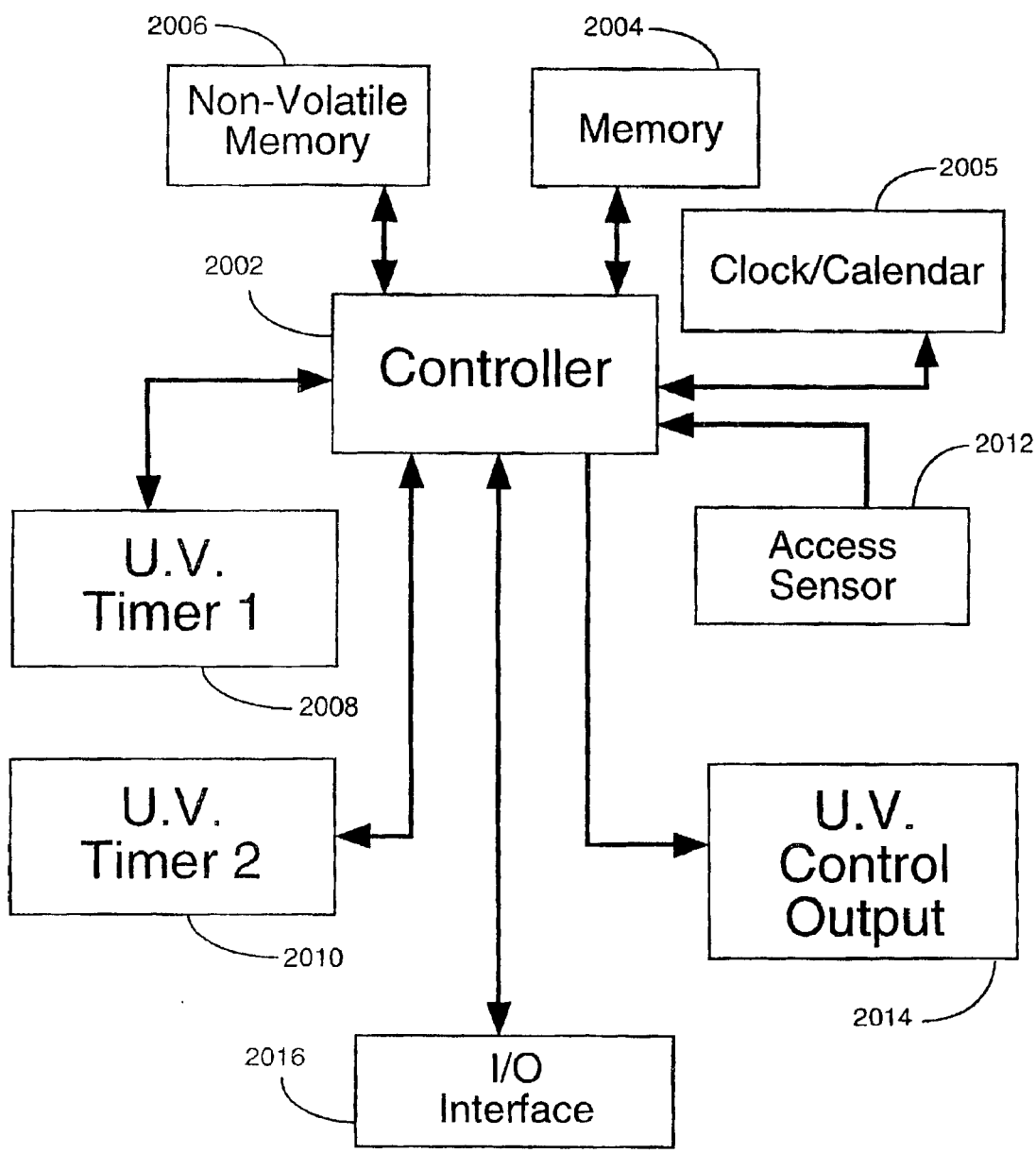
FIG. 20 is an electrical block diagram illustrating an exemplary control system for a storage system, in accordance with a preferred embodiment of the present invention.
Figure 21:
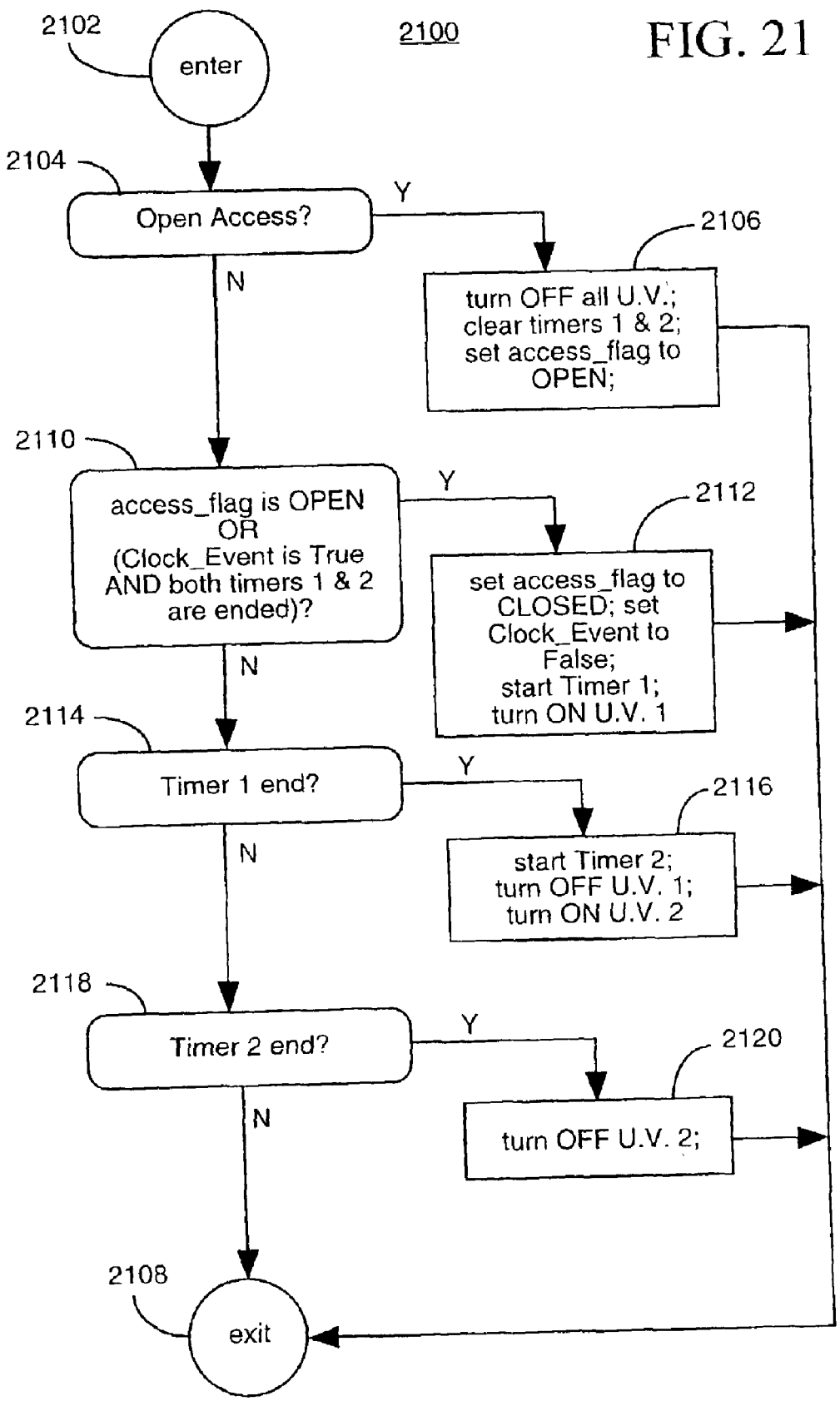
FIG. 21 is an operational flow diagram illustrating an exemplary operational flow sequence for the control system of FIG. 20, in accordance with a preferred embodiment of the present invention.
Figure 22:
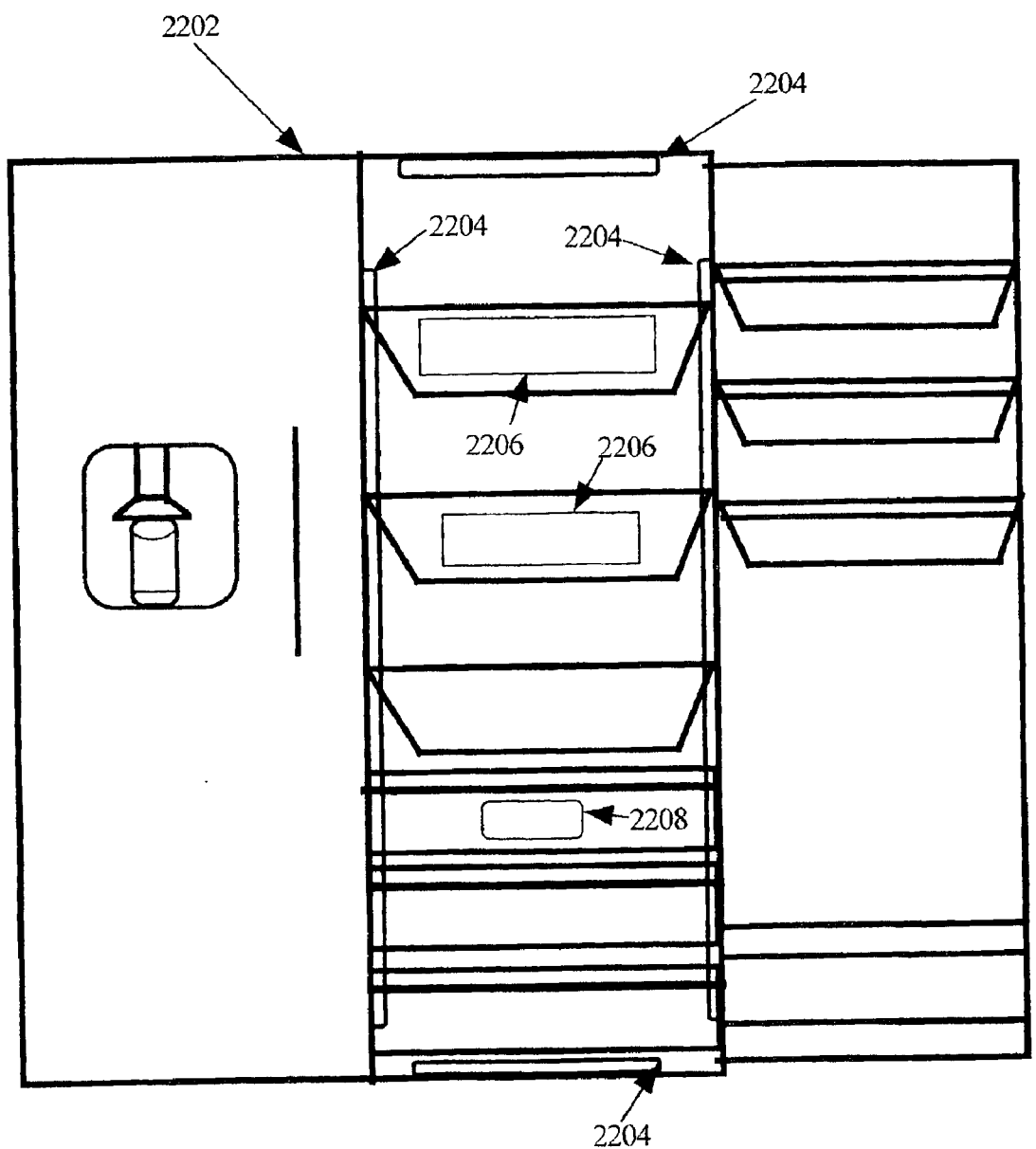
FIG. 22 is a front view of a side-by-side refrigerator and freezer storage system illustrating an exemplary embodiment of the storage system discussed with reference to FIGS. 20 and 21, according to the preferred embodiments of the present invention.

Referring to FIGS. 20, 21, and 22, and exemplary product storage system is illustrated according to a preferred embodiment of the present invention. Product storage take many forms. For example, a freezer or refrigeration system, such as illustrated in FIG. 22, can store product within shelves or storage bins to great lengths of time before consumption or use of the products and/or objects 2206, 2208. As illustrated in FIG. 22, products and/or objects are stored in a rigid type container 2206 or in a flexible type container 2208. In either case, the products are typically stored on shelves and/or storage bins or drawers that are contained within the storage system, such as the freezer or refrigeration system as shown in FIG. 22. The refrigerator 2202 in FIG. 22 includes ultraviolet radiation energy sources 2204 that are strategically located inside the internal compartments of the refrigerator 2202 to radiate ultraviolet energy that will substantially expose all surfaces of the contained products and/or objects 2206,2208 in the refrigerator 2202. Additionally, the environment and atmosphere surrounding the products and/or objects, 2206, 2208, will also be exposed to the ultraviolet radiation energy from the U.V. Sources 2204. The refrigerator 2202, in this example, is shown as a side-by-side refrigerator with one of it's doors open to show the internal compartments of the refrigerator at the open side while the left side of the refrigerator 2202 remains closed. Note that it is very common for refrigerator systems 2202, to include a normal incandescent lamp within the container in the refrigerator 2202 such that when the door opens to allow access to the internal compartments of the refrigerator 2202 the incandescent lamp turns ON to illuminate and allow a user to see the products and/or objects contained in that compartment in the refrigerator 2202. However, according to a preferred embodiment of the present invention, when a user is about to open and gain access to the internal compartments of a storage system such as the refrigerator 2202, the ultraviolet radiation sources 2204 must be turned OFF to prevent any potential injury to a user when opening the door, and/or gaining access to, the internal compartments of the storage system such as the refrigerator 2202. That is the ultraviolet radiation energy be turned OFF anytime that a user is about to gain access to the internal compartments of the storage system 2202.

As illustrated in FIG. 20, the storage system, according to the present example, comprises electronic controlling circuits 2000. The control system 2000 includes a controller 2002 that is electrically coupled to a memory 2004 and further electrically coupled to a non-volatile memory 2006. The non-volatile memory 2006 maintains storage of data and parameters that persist even when power is removed from the control system 2000. A clock/calendar 2005 is communicatively coupled to the controller 2002 such that it provides date and time information to the controller 2002. Additionally, the controller 2002 is electrically coupled to a first U.V. timer 2008 and a second U.V. timer 2010. In this example, the first U.V. timer 2008 is used by the controller 2002 to keep track of a time interval for turning ON and then OFF a radiated ultraviolet radiation energy at a first frequency, such as at the 253 nm wavelength that typically provides strong anti-microbial effects on the exposed surfaces. The second U.V. timer 2010 is used to keep track of a time interval where ultraviolet radiation energy is radiated at a second frequency, such as at about 185 nm wavelength. This second frequency provides efficient conversion energy for energizably converting the convertible agent comprising oxygen to the sanitizing agent comprising ozone. An access sensor 20212 is communicatively coupled to the controller 2002 for sensing when access to the internal compartments of the storage system is being requested by a user. This access sensor 2012 indicates when a user is about to open the door to the storage system such as the refrigerator 2202. Since it is important to keep ultraviolet radiation energy from radiating when a user has access to the internal compartments of the storage system, the controller 2002 monitors the access sensor 2012 at all times to immediately detect when a user is attempting to gain access to the internal compartments of the storage system. Preferably, the storage system has an additional locking mechanism that will maintain it locked and inaccessible by an external user while a U.V. energy is radiated in the internal compartment of the storage system. That is, the user must request access to gain access to the internal compartments of the storage system before actually gaining the access while ultraviolet radiation energy is being used inside the compartments. Preferably, the access sensor 2012 monitors not only that the door is being opened by a user but monitors a request by a user to open and gain access. For example, a user pulling on the handle of the refrigerator door may request access and the controller 2012 will detect this via the access sensor 2012. However access will only be granted by the controller 2002 when it has affirmatively turned OFF all of the ultraviolet radiation sources inside the compartments of the storage system. The controller 2002 communicates via the IO interface 2016 with locking mechanisms for all the access entry points thereby making sure that access is only gained after the internal compartments are safe for use by the user. Additionally, the controller 2002 controls the ultraviolet radiation sources 2004 via the U.V. control output 2014. The U.V. control output interface 2014 communicates the control signals to the driving circuits for the particular ultraviolet radiation sources 2204. These ultraviolet radiation sources 2204 can be energized to radiate at a first ultraviolet radiation energy such as at the wave length 253 nm, or at a second ultraviolet radiation energy, such as at a wave length of about 185 nm, or the sources 2204 can all be turned OFF. According to the present example, every time that a user opens and then closes the access to the storage system, such as opening and closing the doors to the refrigerator 2202, the controller 2002 operates to cycle between a first ultraviolet radiation energy and followed by a second ultraviolet radiation energy to provide the anti-microbial effects of the first ultraviolet radiation energy to the products and/or objects stored in the storage system and then followed by converting the convertible agent comprising oxygen in the compartments of the storage system and in the packaging of the package products and/or objects 2206, 2208, to the sanitizing agent comprising ozone to provide an extended sanitizing and/or sterilizing effect to the stored products and/or objects in the storage system. Since the sanitizing agent comprising ozone in the compartments contained in the storage system may also be an irritant and/or harmful to the users that are external and attempting to gain access to the internal compartments of the storage system, when the controller 2002 detects that the access sensor 2012 is indicating that a user is requesting access to the internal compartments of the storage system, the controller 2002 may turn OFF all U.V. Sources that are currently operational and then cycle briefly such as for 10 to 30 seconds, the first ultraviolet energy source which operates about the 253 nm wavelength range. This frequency of the ultraviolet radiation energy will essentially convert the sanitizing agent comprising ozone in the compartments in the storage system back to the convertible agent comprising oxygen which then presents no harmful effects to the user. After this cycle with the substantially 253 nm wavelength range ultraviolet radiation energy, the controller 2002 can safely allow access to the external user to gain access to the internal compartments of the storage system. The controller 2002 can provide a signal via the IO interface 2016 to release the locking mechanism of the access point, such as the door to the refrigerator 2202 to then allow the user to completely open and gain access to the internal compartment of the refrigerator 2202.

According to a preferred embodiment of the present invention, the controller 2002 and generally the control system 2000 operates according to the operational sequence illustrated in FIG. 21. The controller 2002 operates according to the exemplary operational sequence 2100 such as in a multi-tasking interrupt driven system where the sequences entered, at step 2102, and then exited, at step 2108, during each pass that the controller 2002 is monitoring conditions for the storage system. This monitoring can require that the exemplary operational sequence 2100 be followed many times a second, such as every 40 or 50 ms. The controller 2002, at step 2104, monitors whether a user is requesting access to the internal compartments of the storage system. If the request occurred and have been granted, at step 2104, then the controller 2002 turns OFF all ultraviolet radiation energy sources clears the times 1 and 2 and sets the access flag to open which indicates that the user has gained access to the internal compartments of the storage system. While the user has access to the internal compartments of the storage system, at step 2104, all ultraviolet radiation sources will be maintained in the OFF. When the user closes the door to the storage system and there is no more open access by an external user, at step 2104, then the controller 2002 checks whether the access flag is set to open at step 2110. This indicates that the door has just been closed for the first time after a user has gained access to the internal compartment of the storage system. Alternatively, if a clock event is set to true that indicates that the clock calendar has reached a point where it has scheduled for cycling to occur between the first ultraviolet radiation energy and the second ultraviolet radiation energy inside the compartment in the storage system. This even can occur for example, once per day or once every few days or even much more frequently. Preferably, the time for the clock event is set in the late evening or midnight when users are not likely to be opening and gaining access to the storage system. Therefore, if the clock event is true and both timers 1 and 2 are ended, which indicates that the system is in idle mode and that no ultraviolet radiation energy source is operational at the time, then the clock event is also a triggering event for beginning a cycling process for the ultraviolet radiation energy sources in the compartment in the storage system. The controller 2002, at step 2112, then sets the access flag to close and then sets the clock event to false. The controller 2002 then starts the timer 1 to cycle for the time interval desired for energizing the first ultraviolet radiation energy source and then turns ON the first ultraviolet radiation energy sources. This time, for example, can last from 10 to 30 seconds or alternatively a much longer time interval like a few minutes. When the first timer has ended, at step 2114, then the controller 2002, at step 2116, starts the second timer, turns OFF the first ultraviolet energy source, and then turns ON the second ultraviolet energy source. When the second timer has ended, at step 2118, the controller 2002 turns OFF the second ultraviolet energy source, at step 2120. In this way, the controller 2002 for the storage system cycles the first and second ultraviolet energy sources every time that a user closes the door to the refrigerator 2202, or completes access to the internal compartments of the storage system, and additionally a clock event allows a cycling during those times when the storage system is closed and it is desired to provide additional sanitizing and/or sterilizing effect to the stored and packaged products and/or objects in the internal compartment of the storage system. In this way, the sanitizing and/or sterilizing effect for the products and/or objects stored in the storage system can be significantly extended thereby enhancing the sanitary and/or sterile product condition as well as extending the life of the products as while in storage system. This is a significant advantage of the present invention that is not available from any known prior art system.

Although specific embodiments of the invention have been disclosed, it will be understood by those having ordinary skill in the art that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention.

What is claimed is:

1. A system comprising:
   a packaging container for receiving products and/or objects therein, the packaging container comprising at least one storage volume, the at least one storage volume containing a first agent that is energizably convertible by an energy source to a sanitizing agent comprising ozone in the at least one storage volume, the sanitizing agent comprising ozone being transferable from the at least one storage volume to the products and/or objects to provide at least one of a sanitizing, disinfecting, and sterilizing, application to the products and/or objects; and
   means for providing rotational motion to the products and/or objects being stored in one of the at least one storage volume for exposing surfaces of the products and/or objects to the sanitizing agent comprising ozone.

2. The system of claim 1, wherein the energy source comprises an ultraviolet energy radiation energy source for radiating U.V. energy in the at least one storage volume.

3. The system of claim 1, wherein the means for providing rotational motion provides the rotational motion to the products and/or objects being stored in one of the at least one storage volume for exposing surfaces of the products and/or objects to at least one of radiation energy of an energy source and sanitizing agent comprising ozone.

4. The system of claim 3, wherein the energy source comprises an ultraviolet energy radiation energy source for radiating U.V. energy in the at least one storage volume.

5. The system of claim 1, wherein the means for providing rotational motion comprises at least one of:
   an incline for providing rotational motion to products and/or objects being stored in one of the at least one storage volume;
   a rough and/or ridged surface for providing rotational motion to products and/or objects moving over the surface while being stored in one of the at least one storage volume;
   at least one friction strip for providing rotational motion to products and/or objects moving over the friction strip while being stored in one of the at least one storage volume; and
   a baffle structure for providing rotational motion to products and/or objects moving through the baffle structure while being stored in one of the at least one storage volume.

6. The system of claim 1, wherein the first agent comprises oxygen and the first agent is energizably convertible to the sanitizing agent comprising ozone by the energy source at a first state of the energy source, and wherein the sanitizing agent comprising ozone is energizably convertible to the first agent comprising oxygen by the energy source at a second state of the energy source.

7. The system of claim 1, wherein the energy source comprises
   a first ultraviolet radiation energy source to radiate a first ultraviolet radiation energy to energizably convert the first agent comprising oxygen to the sanitizing agent comprising ozone; and
   a second ultraviolet radiation energy source to radiate a second ultraviolet radiation energy that delivers antimicrobial ultraviolet energy to exposed surfaces of the products and/or objects being stored in one of the at least one storage volume.

8. The system of claim 7, wherein the first ultraviolet radiation energy source radiates first ultraviolet radiation energy at about a 185 nanometer wavelength range, and wherein a second ultraviolet radiation energy source radiates second ultraviolet radiation energy at about a 253 nanometer wavelength range.

9. The system of claim 1, wherein the packaging container is at least partially transparent to ultraviolet radiation, and
   wherein the energy source comprises an ultraviolet radiation energy source to radiate ultraviolet radiation energy through at least a portion of the packaging container to energizably covert the first agent to the sanitizing agent comprising ozone in the at least one store.

10. The system of claim 1, wherein the packaging container is at least partially transparent to ultraviolet radiation, and wherein the packaging container comprises at least one of a plastic film, a polymer film, a liner structure, a bag, a rigid container, a box container, and a cylinder container.

11. A system comprising:
    a storage volume for storing products and/or objects, the storage volume containing a first agent that is energizably convertible by an energy source to a sanitizing agent comprising ozone;
    an access port for a user to access the storage volume to store in, and/or remove products and/or objects from, the storage volume;
    an access sensor for sensing when a user is requesting access of the access port to access the storage volume;
    at least one energy source for controllably radiating energy in the storage volume to provide at least one of a sanitizing, disinfecting, and sterilizing, application to the products and/or objects in the storage volume; and a control system, communicatively coupled to the access sensor and to the at least one energy source, for sensing when a user is accessing the access port and for controlling the at least one energy source, the at least one energy source being controlled in OFF state while a user is accessing the access port to access the storage volume.

12. The system of claim 11, wherein the at least one energy source comprises a first ultraviolet radiation energy source to radiate a first ultraviolet radiation energy to energizably convert a first agent comprising oxygen to a sanitizing agent comprising ozone in the storage volume and/or in a packaged storage volume containing products and/or objects in packaging that is stored in the storage volume for storing products and/or objects; and a second ultraviolet radiation energy source to radiate a second ultraviolet radiation energy that delivers antimicrobial ultraviolet energy to exposed surfaces of the products and/or objects being stored in the storage volume and/or to exposed surfaces of products and/or objects being stored in packaged storage volume containing products and/or objects in packaging that as stored in the storage volume for storing products and/or objects.

13. The system of claim 12, wherein the packaging that is stored in the storage volume is substantially transparent to the first and second ultraviolet radiation energy to allow the ultraviolet radiation energy in the packaged storage volume containing products and/or objects in the packaging.

14. The system of claim 12, wherein the first ultraviolet radiation energy source radiates first ultraviolet radiation energy at about a 185 nanometer wavelength range, and wherein a second ultraviolet radiation energy source radiates second ultraviolet radiation energy at about a 253 nanometer wavelength range.

15. The system of claim 11, wherein the control system determines when the storage volume is not being accessed by a user, and, in response thereto, enables at least for a predetermined time interval the at least one energy source to be controlled in ON state for controllably radiating energy in the storage volume to provide at least one of a sanitizing, disinfecting, and sterilizing, application to the products and/or objects in the storage volume.

16. The system of claim 11, wherein the control system determines when the storage volume is first not being accessed by a user after a user has been accessing the access port to access the storage volume, and, in response thereto, enables for a predetermined time interval the at least one energy source to be controlled in ON state followed by OFF state for controllably radiating energy in the storage volume to provide at least one of a sanitizing, disinfecting, and sterilizing, application to the products and/or objects in the storage volume.

17. The system of claim 11, wherein the control system comprises a clock/calendar module for providing clock events that indicate a schedule for predetermined time intervals for controllably radiating energy in the storage volume, and wherein the control system determines when the storage volume is not being accessed by a user and a clock event has occurred, and, in response thereto, enables at least for a predetermined time interval the at least one energy source to be controlled in ON state followed by OFF state according to the schedule for controllably radiating energy in the storage volume to provide at least one of a sanitizing, disinfecting, and sterilizing, application to the products and/or objects in the storage volume.

18. A method comprising:

rotationally providing products and/or objects in a packaging storage volume to substantially expose surfaces of the products and/or objects to at least one of a sanitizing, disinfecting, and sterilizing, application in the packaging storage volume; and radiating ultraviolet energy in the packaging storage volume to energizably convert a first agent comprising oxygen to a sanitizing agent comprising ozone in the packaging storage volume to provide at least one of a sanitizing, disinfecting, and sterilizing, application to the products and/or objects.

19. The method of claim 18, wherein ultraviolet energy is radiated in the packaging storage volume to deliver antimicrobial ultraviolet energy to exposed surfaces of the products and/or objects being stored in the packaging storage volume.

20. The method of claim 18, wherein ultraviolet energy is radiated in the packaging storage volume at a first frequency about 253 nanometer wavelength range to deliver antimicrobial ultraviolet energy to exposed surfaces of the products and/or objects being stored in the packaging storage volume, and wherein ultraviolet energy is radiated in the packaging storage volume at a second frequency about 185 nanometer wavelength range to energizably convert a first agent comprising oxygen to a sanitizing agent comprising ozone in the packaging storage volume.

21. The system of claim 11, wherein the control system, being communicatively coupled to the access sensor and to the at least one energy source, for sensing when a user is requesting access of the access port to access the storage volume, and, in response thereto, for maintaining the access port locked preventing user access to the storage volume while the at least one energy source is determined to be in an ON state.

22. The system of claim 21, wherein the control system for sensing when a user is requesting access of the access port to access the storage volume, and, in response thereto, maintaining the access port locked to prevent user access to the storage volume while enabling the at least one energy source to be controlled in ON state followed by OFF state for controllably radiating ultraviolet radiation energy at about a 253 nanometer wavelength range in the storage volume to convert sanitizing agent comprising ozone in the storage volume to an agent comprising oxygen, and thereafter releasing a lock of the access port to allow the user access to the storage volume.

* * * * *